(12) United States Patent
Seward

(10) Patent No.: US 10,617,678 B2
(45) Date of Patent: Apr. 14, 2020

(54) TREATMENT OF RESTENOSIS USING TEMSIROLIMUS

(71) Applicant: MERCATOR MEDSYSTEMS, INC., Emeryville, CA (US)

(72) Inventor: Kirk Patrick Seward, San Francisco, CA (US)

(73) Assignee: MERCATOR MEDSYSTEMS, INC., Emeryville, CA (US)

( * ) Notice: Subject to any disclaimer, the term of this patent is extended or adjusted under 35 U.S.C. 154(b) by 0 days.

(21) Appl. No.: 15/890,857

(22) Filed: Feb. 7, 2018

(65) Prior Publication Data

US 2018/0169075 A1 Jun. 21, 2018

Related U.S. Application Data

(63) Continuation of application No. PCT/US2017/052790, filed on Sep. 21, 2017.

(60) Provisional application No. 62/398,471, filed on Sep. 22, 2016.

(51) Int. Cl.
| | |
|---|---|
| *A61K 31/436* | (2006.01) |
| *A61P 9/00* | (2006.01) |
| *A61K 9/00* | (2006.01) |
| *A61P 9/14* | (2006.01) |

(52) U.S. Cl.
CPC .......... *A61K 31/436* (2013.01); *A61K 9/0019* (2013.01); *A61P 9/00* (2018.01); *A61P 9/14* (2018.01)

(58) Field of Classification Search
CPC ........ A61K 9/0019; A61K 31/436; A61P 9/14
See application file for complete search history.

(56) References Cited

U.S. PATENT DOCUMENTS

| | | | |
|---|---|---|---|
| 5,112,305 A | 5/1992 | Barath et al. | |
| 5,196,024 A | 3/1993 | Barath | |
| 5,270,047 A | 12/1993 | Kauffman et al. | |
| 5,354,279 A | 10/1994 | Hoefling | |
| 5,362,718 A | 11/1994 | Skotnicki et al. | |
| 5,527,532 A | 6/1996 | Edelman et al. | |
| 5,538,504 A | 7/1996 | Linden et al. | |
| 5,645,564 A | 7/1997 | Northrup et al. | |
| 5,681,281 A | 10/1997 | Vigil et al. | |
| 5,693,029 A | 12/1997 | Leonhardt | |
| 5,722,989 A | 3/1998 | Fitch et al. | |
| 5,866,561 A | 2/1999 | Ungs | |
| 5,900,246 A | 5/1999 | Lambert | |
| 6,009,877 A | 1/2000 | Edwards | |
| 6,059,815 A | 5/2000 | Lee et al. | |
| 6,102,933 A | 8/2000 | Lee et al. | |
| 6,210,392 B1 | 4/2001 | Vigil et al. | |
| 6,283,947 B1 | 9/2001 | Mirzaee | |
| 6,302,870 B1 | 10/2001 | Jacobsen et al. | |
| 6,334,856 B1 | 1/2002 | Allen et al. | |
| 6,494,862 B1 | 12/2002 | Ray et al. | |
| 6,547,303 B1 | 4/2003 | Anderson | |
| 6,547,803 B2 | 4/2003 | Seward et al. | |
| 6,625,486 B2 | 9/2003 | Lundkvist et al. | |
| 6,860,867 B2 | 3/2005 | Seward et al. | |
| 7,008,411 B1 | 3/2006 | Mandrusov et al. | |
| 7,094,765 B1 | 8/2006 | Iversen et al. | |
| 7,247,149 B2 | 7/2007 | Beyerlein | |
| 7,744,584 B2 | 6/2010 | Seward et al. | |
| 8,708,995 B2 | 4/2014 | Seward et al. | |
| 9,884,013 B2* | 2/2018 | Seward | A61K 47/6931 |
| 2002/0001581 A1 | 1/2002 | Lynch et al. | |
| 2002/0052404 A1 | 5/2002 | Hunter et al. | |
| 2002/0156000 A1 | 10/2002 | May et al. | |
| 2002/0188310 A1 | 12/2002 | Seward et al. | |
| 2003/0040712 A1 | 2/2003 | Ray et al. | |
| 2003/0078562 A1 | 4/2003 | Makower et al. | |
| 2003/0120297 A1 | 6/2003 | Beyerlein | |
| 2003/0170287 A1 | 9/2003 | Prescott | |
| 2003/0171734 A1 | 9/2003 | Seward et al. | |
| 2004/0067197 A1 | 4/2004 | Leclerc et al. | |
| 2004/0138643 A1 | 7/2004 | Seward et al. | |
| 2004/0162542 A1 | 8/2004 | Wilber et al. | |
| 2004/0167152 A1* | 8/2004 | Rubino | A61K 9/0019 514/291 |
| 2004/0260240 A1 | 12/2004 | Beyerlein | |
| 2004/0260268 A1 | 12/2004 | Falotico et al. | |
| 2005/0090714 A1 | 4/2005 | Greff | |
| 2005/0158361 A1 | 7/2005 | Dhondt et al. | |
| 2005/0163711 A1 | 7/2005 | Nycz et al. | |
| 2005/0182071 A1 | 8/2005 | Seward et al. | |

(Continued)

FOREIGN PATENT DOCUMENTS

| | | |
|---|---|---|
| WO | WO-0121157 A2 | 3/2001 |
| WO | WO-0121157 A3 | 12/2001 |

(Continued)

OTHER PUBLICATIONS

International Application No. PCT/US17/52790 International Search Report and Written Opinion dated Dec. 8, 2017.
Siablis, D. et al. Sirolimus-Eluting Versus Bare Stents After Suboptimal Ingrapopliteal Angioplastry for Critical Limb Ischemia: Enduring 1-Year Angiographic and Clinical Benefit, J. Endovasc. Ther. 14:241-250 (2007).
Co-pending U.S. Appl. No. 15/990,167, filed May 25, 2018.
Altman et al., Exploring heart lymphatics in local drug delivery, Lymph. Res. Biol., (2003) 1:47-54.
Barath et al., "Infiltrator Angioplasty Balloon Catheter: a device for combined angioplasty and intramural site-specific treatment," Cathet Cardiovasc Diagn. Jul. 1997;41(3):333-341.
Chandrasekar et al., "Coronary Artery Endothelial. Protection After Local Delivery of 17ll-Estradiol During Balloon Angioplasty in a Porcine Model : A Potential New Pharmacologic Approach to Improve Endothelial Function," J. Am. Col. Cardiol. (2001), 38(5):1570-1576.

(Continued)

Primary Examiner — James D. Anderson
(74) Attorney, Agent, or Firm — Wilson Sonsini Goodrich & Rosati

(57) ABSTRACT

Described herein are methods for distributing temsirolimus to a tissue surrounding a blood vessel for treating vascular diseases. Also disclosed are injectable compositions of temsirolimus for delivery into the tissue surrounding a blood vessel for treating vascular diseases.

51 Claims, 14 Drawing Sheets

(56) References Cited

U.S. PATENT DOCUMENTS

| | | |
|---|---|---|
| 2005/0232965 A1 | 10/2005 | Falotico |
| 2006/0069349 A1 | 3/2006 | Ganz et al. |
| 2006/0115903 A1 | 6/2006 | Ridker et al. |
| 2006/0122684 A1 | 6/2006 | Lye et al. |
| 2006/0189941 A1 | 8/2006 | Seward et al. |
| 2007/0078620 A1 | 4/2007 | Seward et al. |
| 2007/0100318 A1 | 5/2007 | Seward et al. |
| 2007/0100319 A1 | 5/2007 | Seward et al. |
| 2007/0100320 A1 | 5/2007 | Seward et al. |
| 2007/0106248 A1 | 5/2007 | Seward et al. |
| 2007/0106249 A1 | 5/2007 | Seward et al. |
| 2007/0106250 A1 | 5/2007 | Seward et al. |
| 2007/0106251 A1 | 5/2007 | Seward et al. |
| 2007/0106252 A1 | 5/2007 | Seward et al. |
| 2007/0106253 A1 | 5/2007 | Seward et al. |
| 2007/0106254 A1 | 5/2007 | Seward et al. |
| 2007/0106255 A1 | 5/2007 | Seward et al. |
| 2007/0106256 A1 | 5/2007 | Seward et al. |
| 2007/0106257 A1 | 5/2007 | Seward et al. |
| 2007/0129789 A1 | 6/2007 | Cottone, Jr. et al. |
| 2007/0269385 A1 | 11/2007 | Yun et al. |
| 2008/0038316 A1 | 2/2008 | Wong et al. |
| 2009/0204104 A1 | 8/2009 | Tremble et al. |
| 2010/0082095 A1 | 4/2010 | Pacetti et al. |
| 2010/0305546 A1 | 12/2010 | Seward et al. |
| 2013/0029950 A1 | 1/2013 | Bischoff et al. |
| 2013/0035665 A1 | 2/2013 | Chu et al. |
| 2013/0224255 A1* | 8/2013 | Hossainy ............... A61F 2/82 424/400 |
| 2014/0296279 A1* | 10/2014 | Seward ............. A61K 31/436 514/291 |
| 2014/0303569 A1 | 10/2014 | Seward et al. |
| 2015/0141959 A1 | 5/2015 | Kirk |

FOREIGN PATENT DOCUMENTS

| | | |
|---|---|---|
| WO | WO-2010104584 A2 | 9/2010 |
| WO | WO-2014118696 A2 | 8/2014 |
| WO | WO-2017078405 A1 | 5/2017 |

OTHER PUBLICATIONS

Chandrasekar et al., "Local Delivery of 17-Beta-Estradiol Decreases Neointimal Hyperplasia After Coronary Angioplasty in a Porcine Model," J. Am. Col. Cardiol. (2000), 36(6):1972-1978.

ClinicalTrials.gov. Identifier: NCT01507558. Dexamethasone Infusion to the Adventitia to Enhance Clinical Efficacy After Femoropopliteal Revascularization (DANCE). https://clinicaltrials.gov/ct2/show/NCT01507558?term=nct01507558&rank=1. Last updated Aug. 15, 2014. Accessed on Mar. 4, 2015. 4 pages.

Co-pending U.S. Appl. No. 16/058,690, filed Aug. 8, 2018.

Creel, "Arterial Paclitaxel Distribution and Deposition," Circulation Research. Apr. 2000;86:879-884.

Dai-Do et al., "17 beta-estradiol inhibits proliferation and migration of human vascular smooth muscle cells: similar effects in cells from postmenopausal females and in males," Cardiovasc Res. Nov. 1996;32(5):980-985.

Daschner et al., Penetration of gentamicin into heart valves, subcutaneous and muscular tissue of patients undergoing open heart surgery, J. Cardiovasc. Surg., (1986) 581-584.

European Application No. 16743927.2-1109 Extended European Search Report dated Aug. 17, 2018.

Gaspardone, et al. C-Reactive protein, clinical outcome, and restenosis rates after implantation of different drug-eluting stents. Am J Cardiol. May 1, 2006;97(9):1311-6. Epub Mar. 20, 2006.

Gasper, W. et al. Adventitial Nab-Rapamycin Injection Reduces Porcine Femoral Artery Luminal Stenosis Induced by Balloon Angioplasty via Inhibition of Medial Proliferation and Adventitial Inflammation. Circulation: Cardiovascular Interventions. 6(6):701-709 (Dec. 1, 2013).

Han, et al. The favorable clinical and angiographic outcomes of a high-dose dexamethasone-eluting stent: randomized controlled prospective study. Am Heart J. Nov. 2006;152(5):887.e1-7.

Ikeno et al., "Novel percutaneous adventitial drug delivery system for regional vascular treatment," Catheter Cardiovasc. interv., (2004) 63: 220-230.

International Application No. PCT/US18/34713 International Search Report and Written Opinion dated Oct. 19, 2018.

International Application No. PCT/US18/34713 Search Report and Written Opinion dated Oct. 19, 2018.

International search report and written opinion dated Mar. 17, 2016 for PCT/US2016/014819.

International search report dated Apr. 21, 2004 for PCT/US2003/002130.

Konig, et al. Randomized comparison of dexamethasone-eluting stents with bare metal stent implantation in patients with acute coronary syndrome: serial angiographic and sonographic analysis. Am Heart J. Jun. 2007;153(6):979.e1-8.

Laham et al., Intracoronary and intravenous administration of basic fibroblast growth factor: myocardial and tissue distribution, Drug Met. Disp., (1999) 27:821-826.

Laham et al., Intrapericardial administration of basic fibroblast growth factor: myocardial and tissue distribution and comparison with intracoronary and intravenous administration, Cath Cardio. Interv., (2003) 58:375-381.

Nikol et al., "Needle Injection Catheter Delivery of the Gene for an Antibacterial Agent Inhibits Neointimal Formation," Gene Therapy, May 1999, vol. 6, No. 5, pp. 737-748.

Notice of allowance dated Feb. 23, 2010 for U.S. Appl. No. 10/691,119.

Notice of allowance dated Apr. 23, 2015 for U.S. Appl. No. 14/203,942.

Notice of allowance dated Dec. 26, 2013 for U.S. Appl. No. 12/790,541.

Office action dated Jan. 9, 2015 for U.S. Appl. No. 14/203,942.
Office action dated Jan. 30, 2007 for U.S. Appl. No. 10/350,314.
Office action dated Feb. 2, 2011 for U.S. Appl. No. 12/790,541.
Office action dated Feb. 26, 2009 for U.S. Appl. No. 10/691,119.
Office action dated Apr. 16, 2008 for U.S. Appl. No. 10/691,119.
Office action dated May 15, 2008 for U.S. Appl. No. 10/350,314.
Office action dated May 16, 2007 for U.S. Appl. No. 10/350,314.
Office action dated Jun. 25, 2007 for U.S. Appl. No. 11/601,290.
Office action dated Jun. 25, 2007 for U.S. Appl. No. 11/607,177.
Office action dated Jun. 27, 2007 for U.S. Appl. No. 11/607,168.
Office action dated Jun. 27, 2007 for U.S. Appl. No. 11/607,170.
Office action dated Jun. 27, 2007 for U.S. Appl. No. 11/607,172.
Office action dated Jun. 27, 2007 for U.S. Appl. No. 11/607,175.
Office action dated Jun. 27, 2007 for U.S. Appl. No. 11/607,176.
Office action dated Jun. 27, 2007 for U.S. Appl. No. 11/607,356.
Office action dated Jul. 2, 2007 for U.S. Appl. No. 11/607,355.
Office action dated Jul. 14, 2006 for U.S. Appl. No. 10/350,314.
Office action dated Jul. 16, 2007 for U.S. Appl. No. 11/607,166.
Office action dated Jul. 16, 2007 for U.S. Appl. No. 11/607,167.
Office action dated Jul. 16, 2007 for U.S. Appl. No. 11/607,178.
Office action dated Jul. 16, 2007 for U.S. Appl. No. 11/607,658.
Office action dated Jul. 17, 2007 for U.S. Appl. No. 11/607,169.
Office action dated Aug. 20, 2008 for U.S. Appl. No. 10/350,314.
Office action dated Aug. 20, 2008 for U.S. Appl. No. 10/691,119.
Office action dated Aug. 24, 2007 for U.S. Appl. No. 10/350,314.
Office action dated Sep. 15, 2009 for U.S. Appl. No. 10/691,119.
Office action dated Oct. 11, 2011 for U.S. Appl. No. 12/790,541.
Office action dated Dec. 12, 2006 for U.S. Appl. No. 10/691,119.

Owens, Christopher D. et al. Safety and feasibility of adjunctive dexamethasone infusion into the adventitia of the femoropopliteal artery following endovascular revascularization. Journal of Vascular Surgery 59(4):1016-1024 (Apr. 2014).

Owens, Christopher D., MD. Pilot Results from Dance: Dexamethasone to the Adventitia to eNhance Clinical Efficacy in PAD. pp. 1-19 (2012).

Pharmacia & Upjohn Company, "Depo-Estradiol," Product/Prescription Information [pamphlet], (Aug. 2000), 6 pages total.

(56) References Cited

OTHER PUBLICATIONS

Schillinger, et al. Balloon angioplasty and stent implantation induce a vascular inflammatory reaction. J Endovasc Ther. Feb. 2002;9(1):59-66.
Solmon et al., "Amiodarone versus a [3-blocker to prevent atrial fibrillation after cardiovascular surgery," AHJ, Nov. 2001; 142(5):811-815.
U.S. Appl. No. 14/605,865 Final Office Action dated Aug. 31, 2017.
U.S. Appl. No. 14/605,865 Non-Final Office Action dated Dec. 28, 2017.
U.S. Appl. No. 14/605,865 Non-Final Office Action dated Sep. 17, 2018.
U.S. Appl. No. 14/605,865 Notice of Allowance dated Jul. 6, 2018.
U.S. Appl. No. 14/605,865 Office Action dated Sep. 22, 2016.
U.S. Appl. No. 09/961,079, filed Sep. 20, 2001.
U.S. Appl. No. 60/356,670, filed Feb. 13, 2002.
Ayers et al., Amiodarone instilled into the canine pericardial sac migrates transmurally to produce electrophysiologic effects and suppress atrial fibrillation. Journal of Cardiovascular Electrophysiology. 7(8):713-721 (1996).
U.S. Appl. No. 15/990,167 Office Action dated Apr. 10, 2019.
U.S. Appl. No. 16/058,690 Office Action dated Aug. 7, 2019.
Zhang et al. Synergistic activity of rapamycin and dexamethasone in vitro and in vivo in acute lymphoblastic leukemia via cell-cycle arrest and apoptosis. Leukemia Research 36(3):342-349 (2012).

\* cited by examiner

TREATMENT OF RESTENOSIS USING TEMSIROLIMUS

CROSS-REFERENCE

This application is a continuation of International Application No. PCT/US2017/052790, entitled "TREATMENT OF RESTENOSIS USING TEMSIROLIMUS, filed Sep. 21, 2017, which claims the benefit of U.S. Provisional Application No. 62/398,471, filed Sep. 22, 2016, the content of each of which is incorporated herein by reference in its entirety.

BACKGROUND

The present disclosure relates generally to medical methods and devices. More particularly, the present disclosure relates to medical methods and kits for distributing temsirolimus in the tissue surrounding a blood vessel.

Blockages can form in blood vessels under various disease conditions. In atherosclerosis, the narrowing of arteries in the body, particularly in the heart, legs, carotid and renal anatomy, can lead to tissue ischemia from lack of blood flow. Mechanical revascularization methods, such as balloon angioplasty, atherectomy, stenting, or surgical endarterectomy, may be used to open the blood vessel and to improve blood flow to downstream tissues. Unfortunately, mechanical revascularization can lead to an injury cascade that causes the blood vessel to stiffen and vessel walls to thicken with a scar-like tissue, which can reduce the blood flow and necessitate another revascularization procedure. There is a great desire to reduce the vessel stiffening and thickening following mechanical revascularization to maintain or improve the patency of the blood vessel.

SUMMARY

There is a great desire to reduce the vessel stiffening and thickening following mechanical revascularization of narrowed blood vessel to maintain or improve the patency of the blood vessel. The present disclosure provides methods and injectable composition for distributing temsirolimus to a tissue surrounding a blood vessel for treating vascular diseases.

In a certain aspect, described herein, is a method of treating a vascular disease in a subject. The method of treating the vascular disease in the subject comprises administering to the subject a therapeutically effective amount of a pharmaceutical composition comprising temsirolimus or its pharmaceutically acceptable salts. In certain embodiments, the composition is administered by direct injection to a disease site. In a certain embodiment, the composition is injected though a catheter with a needle. In a certain embodiment, the composition is injected distal or proximal to the disease site. In a certain embodiment, the composition is injected at least about 2 cm away from the disease site. In a certain embodiment, the composition is injected at or adjacent to the disease site. In a certain embodiment, the composition is administered by injection into a blood vessel. In a certain embodiment, the composition is injected into an adventitial tissue surrounding a blood vessel. In a certain embodiment, the composition is injected into a perivascular tissue surrounding a blood vessel. In a certain embodiment, the blood vessel is an artery. In a certain embodiment, the blood vessel is a vein. In a certain embodiment, the artery is a coronary artery or a peripheral artery. In a certain embodiment, the artery is selected from the group consisting of renal artery, cerebral artery, pulmonary artery, and artery in the leg. In a certain embodiment, the artery is below the knee. In a certain embodiment, the artery is in the leg above the knee. In a certain embodiment, the blood vessel is below-knee popliteal vessel or tibial vessel. In a certain embodiment, the composition is injected into a blood vessel wall. In a certain embodiment, the composition is injected into a tissue surrounding the blood vessel wall.

In certain embodiments, the therapeutically effective amount of temsirolimus is about 1 µg to 50 mg, about 10 µg to 20 mg, or about 25 µg to 10 mg. In certain embodiments, the therapeutically effective amount of temsirolimus is about 0.005 mg to 5 mg per cm, or about 0.025 mg to 1 mg per cm of longitudinal length of the disease site in the blood vessel. In certain embodiments, the injection volume of the composition is about 0.01 ml to about 50 ml, or about 0.5 ml to about 20 ml. In certain embodiments, the injection concentration of temsirolimus is 0.01 mg/mL to 2.0 mg/mL, 0.1 mg/mL to 0.5 mg/mL, or 0.1 mg/mL to 0.4 mg/mL. In certain embodiments, 12 months after administration of the pharmaceutical composition, vessel cross-sectional area at the disease site has decreased no more than 60%, 50%, or 30%, when compared to vessel cross-sectional area at the disease site at the time of administration. In a certain embodiment, the composition further comprises a contrast medium for visualizing the injection. In a certain embodiment, the subject is human.

In certain embodiments, the vascular disease is angina, myocardial infarction, congestive heart failure, cardiac arrhythmia, peripheral artery disease, claudication, or critical limb ischemia. In certain embodiments, the vascular disease is atherosclerosis, bypass graft failure, transplant vasculopathy, vascular restenosis, or in-stent restenosis.

In another aspect, described herein, is an injectable composition comprising temsirolimus or a pharmaceutically acceptable salt thereof, and a pharmaceutically acceptable excipient for use in treating a vascular disease. In a certain embodiment, the composition is suitable for adventitial delivery. In a certain embodiment, the composition is suitable for adventitial delivery in the leg. In a certain embodiment, the composition is suitable for adventitial delivery below the knee. In a certain embodiment, the composition is suitable for adventitial delivery in the leg above the knee. In a certain embodiment, the composition is suitable for adventitial delivery to a below-knee popliteal or tibial vessel. In a certain embodiment, the composition is suitable for direct injection to the vascular disease site. In certain embodiments, the therapeutically effective amount of temsirolimus is about 1 µg to 50 mg, about 10 µg to 20 mg, or about 25 µg to 10 mg. In certain embodiments, the injection volume of the composition is about 0.01 ml to about 50 ml, or about 0.5 ml to about 20 ml. In certain embodiments, the therapeutically effective amount of temsirolimus is about 0.005 mg to 5 mg per cm, or about 0.025 mg to 1 mg per cm of longitudinal length of the disease site in the blood vessel. In certain embodiments, the concentration of temsirolimus is 0.01 mg/mL to 2.0 mg/mL, about 0.1 to 0.5 mg/mL, or about 0.1 mg/mL to about 0.4 mg/mL. In a certain embodiment, the injectable composition is for use in treating, preventing, or inhibiting restenosis in the leg. In a certain embodiment, the injectable composition is for use in treating, preventing, or inhibiting restenosis below the knee. In a certain embodiment, the injectable composition is for use in treating, preventing, or inhibiting restenosis in the leg above the knee. In a certain embodiment, the injectable composition is for use in treating, preventing, or inhibiting restenosis in a below-knee popliteal vessel or tibial vessel. In a certain embodiment, the injectable composition is for use in treating, preventing, or inhibiting restenosis in a femoral vessel. In a certain embodiment, the pharmaceutically acceptable excipient of the injectable composition is 0.9% sodium chloride injection USP, dehydrated alcohol, dl-alpha tocopherol, anhydrous citric acid, polysorbate 80, polyethylene glycol 400, propylene glycol, or a combination thereof.

In another aspect, described herein, is a method of treating a peripheral artery disease in a human subject in need thereof, the method comprising administering to the subject a therapeutically effective amount of a pharmaceutical composition comprising temsirolimus or its pharmaceutically acceptable salts thereof, wherein the composition is administered by direct injection to or near a disease site in a tissue surrounding a wall of a peripheral artery or in the wall of the peripheral artery via a laterally extending injection needle of a catheter advanced through vasculature of the human subject, wherein the amount of the pharmaceutical composition is therapeutically effective to cause patency at the disease site after administration to only minimally decrease or to increase when compared to patency at the disease site at the time of administration. In certain embodiments, the therapeutically effective amount of temsirolimus is about 1 μg to 50 mg, about 10 μg to 20 mg, or about 25 μg to 10 mg. In certain embodiments, the therapeutically effective amount of temsirolimus is about 0.005 mg to 5 mg per cm, or about 0.025 mg to 1 mg per cm of longitudinal length of the disease site in the peripheral artery. In certain embodiments, the injection volume of the composition is about 0.01 ml to about 50 ml, or about 0.5 ml to about 20 ml. In certain embodiments, the injection concentration of temsirolimus is 0.01 mg/mL to 2.0 mg/mL, 0.1 mg/mL to 0.5 mg/mL, or 0.1 mg/mL to 0.4 mg/mL. In certain embodiments, 12 months after administration of the pharmaceutical composition, vessel cross-sectional area at the disease site has decreased no more than 60%, 50%, or 30%, when compared to vessel cross-sectional area at the disease site at the time of administration. In a certain embodiment, the composition further comprises a contrast medium for visualizing the injection. In a certain embodiment, the artery is below the knee. In a certain embodiment, the artery is in the leg above the knee. In a certain embodiment, the blood vessel is below-knee popliteal vessel or tibial vessel.

In another aspect, described herein, is an injectable composition comprising temsirolimus or a pharmaceutically acceptable salt thereof, and a pharmaceutically acceptable excipient for use in treating restenosis in a peripheral artery of a human subject, wherein the composition is suitable for adventitial delivery to the peripheral artery, wherein the composition is suitable for direct injection to a vascular disease site in a tissue surrounding a wall of the peripheral artery or in the wall of the peripheral artery via a laterally extending needle from a catheter advanced through vasculature of the human subject in a therapeutically effective amount effective to cause patency at the disease site after administration to increase or minimally decrease when compared to patency at the disease site at the time of administration. In a certain embodiment, the composition is suitable for adventitial delivery in the leg. In a certain embodiment, the composition is suitable for adventitial delivery below the knee. In a certain embodiment, the composition is suitable for adventitial delivery in the leg above the knee. In a certain embodiment, the composition is suitable for adventitial delivery to a below-knee popliteal or tibial vessel. In certain embodiments, the therapeutically effective amount of temsirolimus is about 1 μg to 50 mg, about 10 μg to 20 mg, or about 25 μg to 10 mg. In certain embodiments, the injection volume of the composition is about 0.01 ml to about 50 ml, or about 0.5 ml to about 20 ml. In certain embodiments, the therapeutically effective amount of temsirolimus is about 0.005 mg to 5 mg per cm, or about 0.025 mg to 1 mg per cm of longitudinal length of the disease site in the blood vessel. In certain embodiments, the concentration of temsirolimus is about 0.01 mg/mL to about 2.0 mg/mL, about 0.1 mg/mL to about 0.5 mg/mL, or about 0.1 mg/mL to about 0.4 mg/mL. In a certain embodiment, the pharmaceutically acceptable excipient is 0.9% sodium chloride injection USP, dehydrated alcohol, dl-alpha tocopherol, anhydrous citric acid, polysorbate 80, polyethylene glycol 400, propylene glycol, or a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

DETAILED DESCRIPTION

Figure 1A:
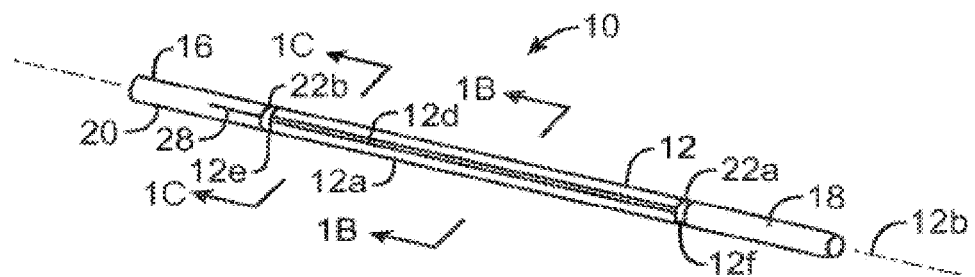
FIG. 1A is a schematic, perspective view of an intraluminal injection catheter suitable for use in the methods and systems of the present disclosure.

The present disclosure describes methods of treating a vascular disease in a subject comprising administering a therapeutically effective amount of a pharmaceutical composition comprising temsirolimus or its pharmaceutically acceptable salts, wherein the composition is administered by direct injection to a disease site.

Blockages can form in blood vessels under various disease conditions. Atherosclerosis, which causes the narrowing, or stenosis, of arteries in the body, particularly in the heart, legs, carotid, and renal anatomy, can lead to tissue ischemia from lack of blood flow. Atherosclerosis in the coronary arteries can cause myocardial infarction, commonly referred to as a heart attack, which can be immediately fatal or, even if survived, can cause damage to the heart which can incapacitate the patient. Other coronary diseases include congestive heart failure, vulnerable or unstable plaque, and cardiac arrhythmias, which cause death and incapacitation. In addition, peripheral artery disease (PAD), where the arteries in peripheral tissues narrow, most commonly affects the leg, renal, and carotid arteries. Blood clots and thrombus in the peripheral vasculature may occlude peripheral blood flow, leading to tissue and organ necrosis. Some patients with PAD experience critical limb ischemia that can result in ulcers and can require amputation in the worst cases. PAD in renal artery can cause renovascular hypertension, and clots in the carotid artery can embolize and travel to the brain, potentially causing ischemic stroke.

To improve blood flow to downstream tissues, various revascularization methods may be used to bypass or open the artery. Artery bypass surgery can be an effective treatment for stenosed, or narrowed, arteries resulting from atherosclerosis and other causes, but it is a highly invasive procedure which is also expensive and requires substantial hospital and recovery time. Mechanical revascularization methods with balloon angioplasty, atherectomy, stenting, or surgical endarterectomy may be used to open, or dilate, the artery. For example, percutaneous transluminal angioplasty (PTA), commonly referred to as balloon angioplasty, is less invasive, less traumatic, and significantly less expensive than bypass surgery. In addition, the effectiveness of balloon angioplasty has improved with the introduction of stenting which involves the placement of a scaffold structure within the artery which has been treated by balloon angioplasty. The stent inhibits abrupt re-closure of the artery and has some benefit in reducing subsequent restenosis resulting from hyperplasia. By salvaging blood vessels rather than bypassing them, more options are left available to physicians in the further treatment of the disease.

Unfortunately, mechanical revascularization procedure can lead to an injury cascade that causes the artery to stiffen and arterial walls to thicken with a scar-like tissue, known as neointimal hyperplasia. Not only can the inner wall of the artery, also known as the intima, thicken and stiffen in response to the injury cascade, but the media, or the middle tissue layer of the wall, and the adventitia, the outer layer of the wall, can thicken and stiffen as well. The thickening, also known as hyperplasia, and the stiffening, also known as sclerosis, can reduce the blood flow to tissues distal to the affected site. As a result, patients who have undergone mechanical revascularization procedure procedures may suffer from a high incidence of restenosis resulting from hyperplasia. Restenosis, or recurrence of stenosis or narrowing, of the blood vessel may necessitate another revascularization procedure to the affected area again.

There is a great desire to reduce the buildup of sclerosis and hyperplasia following mechanical revascularization. Recently, experimental trials have demonstrated that the implanting of stents which have been coated with anti-proliferative drugs can reduce the occurrence of hyperplasia. Mechanical endovascular revascularization alone leads to patency (the binary measure of vessel openness, typically greater than 50% in diameter compared to adjacent non-diseased vessel) rates of 33-55% at one year and 20-50% at two years, while drug-coated balloons and adventitial drug delivery have shown an ability to improve patency to better than 80% at one year and 65-70% at 2 years.

Mechanistic target of rapamycin (mTOR) inhibitors have been identified as promising drugs for coating stents. A member of phosphatidylinositol-3 kinase-related kinase (PIKK) family, mTOR is involved in regulating cell growth, proliferation, cell survival, and angiogenesis. In response to physical insult of revascularization procedure, smooth muscle and endothelial cells in blood vessels can activate stress response pathways, which can lead to cell proliferation, secretion of pro-inflammatory mediators and extracellular matrix components, and ultimately to restenosis. Drugs successful in blocking one or more of the stress response pathways can decrease the degree of restenosis. mTOR inhibitors may reduce cellular proliferation and inflammation and have been used successfully in graft-versus-host disease, in organ transplant and in some cancers by blocking mTOR activation in response to insulin, growth factors and amino acids.

mTOR inhibitors have been generally given names including -limus as their suffix. mTOR inhibitors include the original mTOR inhibitor, sirolimus, also known as rapamycin, and the analogs of sirolimus. These analogs include everolimus, zotarolimus, deforolimus, biolimus and temsirolimus. The -limus drugs were originally approved as immunosuppressants and subsequently, several of the -limus analogs including sirolimus have been approved to treat various cancers. Temsirolimus is approved for the treatment of renal cell carcinoma (RCC), but it is not approved for the treatment of vascular restenosis Temsirolimus, also known as CCI-779, is the only sirolimus analog that is approved in an injectable form. Temsirolimus has a higher water solubility than sirolimus, which allows for intravenous administration. Temsirolimus is a pro-drug for sirolimus, where temsirolimus is metabolized to sirolimus, the active form. Temsirolimus can also be active as an analog and as a prodrug, and can inhibit mTOR and disrupt cell mitosis without being metabolized. This can be important for local delivery for treatment of vascular disease, because there are fewer metabolic reactions in the vascular tissue than in the liver, where the drug is metabolized when administered systemically.

Vascular treatment devices coated with mTOR inhibitors have been in development. Sirolimus, everolimus, and zotarolimus have been coated onto stents. Sirolimus has also been in development for release from a drug-coated balloon in nanoparticle formulation. Other -limus drugs are also being developed for drug-coated balloon release into the inner surface of the endothelial wall of blood vessels.

As an alternative to stent-based luminal drug delivery, the direct delivery of drug into vascular and other luminal walls has been proposed. It would be beneficial to provide methods which enhance the therapeutic concentrations of the pharmaceutical agents in targeted tissues. For example, it would be particularly desirable if the methods could provide for an extended volumetric distribution of the delivered pharmaceutical agent including both longitudinal and radial spreading from the injection site(s) in order to provide therapeutic dosage levels of the agent within the targeted tissue region. It would be further beneficial if the methods could efficiently deliver the drugs into the targeted tissue and limit or avoid the loss of drugs into the luminal blood flow. It would be still beneficial if the persistence of such therapeutic concentrations of the pharmaceutical agent in the tissue were also increased, particularly in targeted tissues away from the blood vessel wall, including the adventitial tissue surrounding the blood vessel wall. Additionally, it would be beneficial to increase the uniformity and extent of pharmaceutical agent delivery over remote, extended, and distributed regions of the adventitia and other tissues surrounding the blood vessels. In some instances, it would be beneficial to provide methods which permit the delivery of pharmaceutical agents through the blood vessel walls at non-diseased sites within the blood vessel, where the agent would then be able to migrate through the adventitia or other tissues to the diseased site(s). Still further, it would be desirable if such intravascular delivery of pharmaceutical agents would be useful for treating diseases and conditions of the tissues and organs in addition to those directly related to the vasculature.

Subjects treated by the methods disclosed herein can exhibit a vascular disease. In one example, the vascular disease may be atherosclerosis in the heart, legs, carotid, or renal blood vessels. In another example, the vascular disease may be peripheral artery disease (PAD). In another example, the vascular disease may be angina, myocardial infarction, congestive heart failure, cardiac arrhythmia, peripheral artery disease, claudication, or critical limb ischemia. In another example, the vascular disease may be atherosclerosis, bypass graft failure, transplant vasculopathy, in-stent restenosis, or restenosis. In one example, the vascular disease may be blood clots, thrombus, or other blockages in a blood vessel that may occlude peripheral blood flow, leading to tissue and organ necrosis. In one example, the vascular disease may be PAD in renal artery or carotid artery. In some examples, the subject with restenosis may have had a procedure to improve the patency of the blood vessel or a revascularization procedure previously.

The disease site of the vascular disease may include blood vessels and the tissues surrounding the blood vessel. The vasculature of a subject refers to the circulatory system and may comprise arterial system, venous systems, or both arterial and venous systems and the blood vessels within those systems. In some examples, the blood vessel may be an artery, arteriole, or other blood vessels of the arterial system. In some examples, the blood vessel may be a vein, venule, or other blood vessels of the venous system. In one example, the artery may be a coronary artery or a peripheral artery. In one example, the artery may be below the knee. In another example, the artery may be in the leg above the knee. In another example, the blood vessel may be below-knee popliteal vessel or tibial vessel. In some examples, the blood vessel may be a femoral vessel. In some examples, the artery may be renal artery, carotid artery, cerebral artery, pulmonary artery, or artery in the leg. In some examples, the artery may be a femoral artery.

Restenosis may be in various tissues and blood vessels in the body. In some instances, the restenosis may be in a peripheral artery. In some instances, the restenosis may be in the leg. In other instances, the restenosis may be below the knee or in the leg above the knee. In some instances, the restenosis may be in a below-knee popliteal vessel or tibial vessel. In some instances, the restenosis may be in a femoral vessel. In other instances, the restenosis may be in a femoral artery.

In some instances, the tissue surrounding a blood vessel may refer to any tissues outside the endothelial cell wall of the blood vessel that is radially away from the lumen of the blood vessel in a cross section and may include plaque and calcification. In some instances, the tissue surrounding a blood vessel may comprise adventitial tissue, perivascular tissue, or any tissue surrounding the endothelial wall of a blood vessel. In some instances, adventitial tissue is also known as adventitia or tunica adventitia or tunica externa. In some instances, adventitial tissue may be outside of the external elastic membrane. In some instances, the tissue surrounding a blood vessel may be tissues outside the tunica intima of the blood vessel. In some instances, the tissue surrounding a blood vessel may be tissues outside the tunica media of the blood vessel. In some instances, the tissue surrounding a blood vessel may be tissues outside the internal elastic membrane. In some instances, the tissue may be a connective tissue. In some instances, the tissue may be diseased tissue such as plaque, fibrosis, calcification, or combinations of diseased and healthy tissues.

In some instances, patency may refer to blood vessel openness. In some instances, patency at the disease site may refer to patency of the blood vessel, or blood vessel openness, at the disease site. In some instances, vessel cross-sectional area at the disease site may refer to patency of the blood vessel at the disease site. In some instances, vessel cross-sectional area may be determined by angiography. In some instances, the angiography may be quantitative vascular angiography (QVA). In other instances, vessel cross-sectional area may be determined by intravascular ultrasound (IVUS). In some instances, patency may be described as percent of diameter of the lumen of the blood vessel that is open and unobstructed. In some instances, patency may be described as percent of cross sectional area of the lumen of the blood vessel, or vessel cross-sectional area, that is open and unobstructed. In other instances, patency may percent of luminal volume that is open and unobstructed. In some instances, patency may require determination of the boundaries of the endothelial wall of the blood vessel. In some instances, a blood vessel that is completely open and unobstructed may have 100% patency; i.e., the blood vessel has a cross-sectional area that is healthy and typical of a normal, healthy blood vessel in the same part of the body. In some instances, a blood vessel that is completely blocked and obstructed may have 0% patency. In some instances, patency is the binary measure of openness greater than 50% in diameter compared to adjacent non-diseased vessel. In some instances, patency is the binary measure of openness greater than 50% in cross-sectional area compared to adjacent non-diseased vessel. In some instances, patency is the binary measure of openness greater than 50% in luminal volume compared to adjacent non-diseased vessel.

In some instances, therapeutically effective may refer to increasing vessel cross-sectional area at the disease site. In some instances, therapeutically effective may refer to increasing the vessel cross-sectional area at the disease site after administration of a pharmaceutical composition. In some instances, therapeutically effective may refer to minimally decreasing the vessel cross-sectional area at the disease site after administration when compared to the vessel cross-sectional area at the disease site at the time of administration. In some instances, therapeutically effective may refer to increasing the vessel cross-sectional area at the disease site. In some instances, therapeutically effective may refer to increasing minimally the vessel cross-sectional area at the disease site after administration when compared to the vessel cross-sectional area at the disease site at the time of administration. In some instances, therapeutically effective may refer to decreasing the vessel cross-sectional area at the disease site no more than 30%, 20%, 10%, or 0% when compared to the vessel cross-sectional area at the disease site at the time of administration; in other words the patency may decrease no more than 30%, 20%, 10%, or 0% when compared to the patency at the disease site at the time of administration. In some instances, the vessel cross-sectional area at the disease site may decrease no more than 60%, 50%, 40%, 30%, 20%, or 10% when compared to vessel cross-sectional area at the disease site at the time of administration. In some instances, the vessel cross-sectional area at the disease site may increase at least 60%, 50%, 40%, 30%, 20%, or 10% when compared to vessel cross-sectional area at the disease site at the time of administration.

The pharmaceutical composition to treat the vascular disease may comprise temsirolimus or its pharmaceutically acceptable salts thereof. In some instances, temsirolimus may be Torisel®. In some instances, the pharmaceutical compositions may further comprise 0.9% sodium chloride injection USP, dehydrated alcohol, dl-alpha tocopherol, anhydrous citric acid, polysorbate 80, polyethylene glycol 400, propylene glycol, or a combination thereof. In some instances, the pharmaceutical compositions may comprise pharmaceutically acceptable excipients. In some instances, the pharmaceutical compositions may comprise other excipients commonly used in injectable compositions. In some instances, the pharmaceutical compositions may comprise a contrast agent to aid in visualization of the delivery of the pharmaceutical composition. In some instances, the pharmaceutical compositions may be injectable. In some instances, the pharmaceutical compositions may be a liquid, a suspension, a solution, or a gel.

In some instances, the pharmaceutical composition may be injected at various locations at or near the disease site. In some instances, the disease site may refer to a blood vessel affected by a vascular disease. In some instances, the disease site may refer to a blood vessel with a partial or complete blockage of the lumen. In some instances, the disease site may refer to a blood vessel with a vessel cross-sectional area of less than 100%, 90%, 80%, 70%, 60%, 50%, 40%, 30%, 20%, or 10% of vessel cross-sectional area of an unobstructed vessel as determined from the vessel wall. In some instances, the pharmaceutical composition may be injected distal or proximal to the disease site. In some instances, the pharmaceutical composition may be injected at least about 2 cm away from the disease site. In some instances, the pharmaceutical composition may be injected at or adjacent to the disease site. In some instances, the pharmaceutical composition may be injected into a blood vessel. In some instances, the pharmaceutical composition may be injected into an adventitial tissue surrounding a blood vessel. In some instances, the pharmaceutical composition may be injected into a perivascular tissue surrounding a blood vessel.

Temsirolimus may have a range of doses that are therapeutically effective for treating the vascular disease. In some instances, the therapeutically effective amount of temsirolimus may be about 1 µg to 50 mg, about 10 µg to 20 mg, about 25 µg to 10 mg, about 1 µg to 2 mg, about 10 µg to 500 µg, about 100 µg to 1 mg, or about 100 µg to 500 µg. In some instances, the therapeutically effective amount of temsirolimus may be about 10 µg, about 25 µg, about 50 µg, about 100 µg, about 500 µg, about 1.0 mg, about 5.0 mg, about 10.0 mg, or about 15.0 mg. In some instances, the therapeutically effective volume of temsirolimus may be about 0.01 ml to about 50 ml, about 0.5 ml to about 20 ml, about 0.5 ml to about 25 ml, about 0.5 ml to about 5 ml, or about 1 ml to about 5 ml. In some instances, the therapeutically effective concentration of temsirolimus may be about 0.1 mg/mL to about 0.4 mg/mL, about 0.1 mg/mL to about 0.5 mg/mL, or about 0.01 mg/mL to about 2.0 mg/mL. In some instances, the therapeutically effective concentration of temsirolimus may be about 0.1 mg/mL, about 0.2 mg/mL, about 0.3 mg/mL, about 0.4 mg/mL, about 0.5 mg/mL, about 1.0 mg/ml, about 1.5 mg/ml, about 2.0 mg/ml, about 2.5 mg/ml, or 3.0 mg/ml. In some instances, the therapeutically effective amount of temsirolimus may be about 0.005 mg to 5 mg per cm of longitudinal length of the disease site in the blood vessel, about 0.025 mg to 1 mg per cm of longitudinal length of the disease site in the blood vessel, about 0.05 mg to 2 mg per cm of longitudinal length of the disease site in the blood vessel, or about 0.1 mg to 1 mg per cm of longitudinal length of the disease site in the blood vessel. The longitudinal length of the disease site in the blood vessel, also known as the longitudinal length of the lesion, may be about 1 cm, 5 cm, 10 cm, 20 cm, 30 cm, 40 cm, or 50 cm.

Drug injection or infusion catheters and devices may be suitable for use with the methods described herein to inject pharmaceutical compositions into blood vessels the treat restenosis. An example of a device includes the Mercator Bullfrog® Micro-Infusion Device available from Mercator MedSystems of Emeryville, Calif. Other examples include the devices described in U.S. patent application Ser. Nos. 14/605,865 and 15/691,138, the entire disclosures of which are incorporated herein by reference. Examples of suitable devices and their use are described as follows.

Figure 1B:
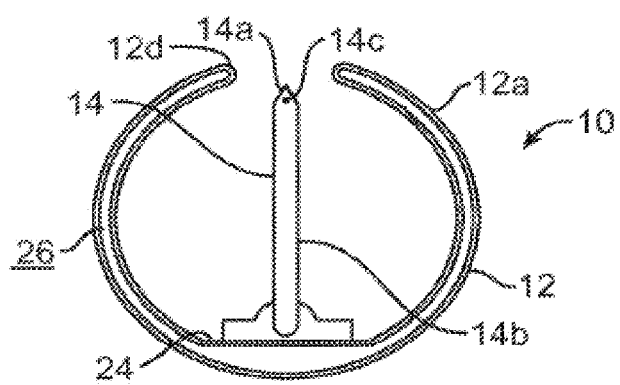
FIG. 1B is a cross-sectional view along line 1B-1B of FIG. 1A.
Figure 1C:
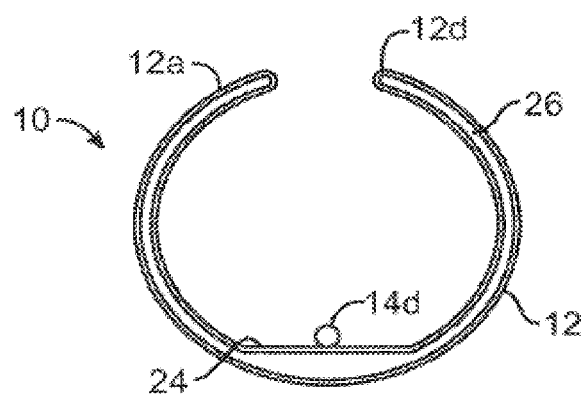
FIG. 1C is a cross-sectional view along line 1C-1C of FIG. 1A.
Figure 2A:
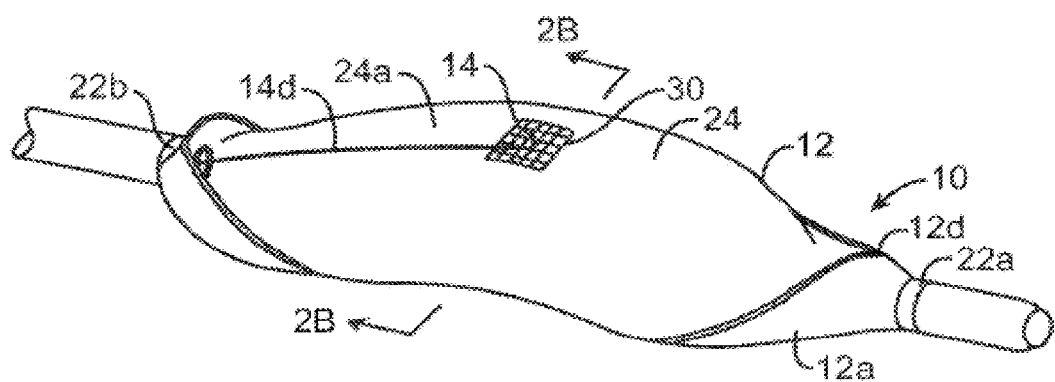
FIG. 2A is a schematic, perspective view of the catheter of FIGS. 1A-1C shown with the injection needle deployed.
Figure 2B:
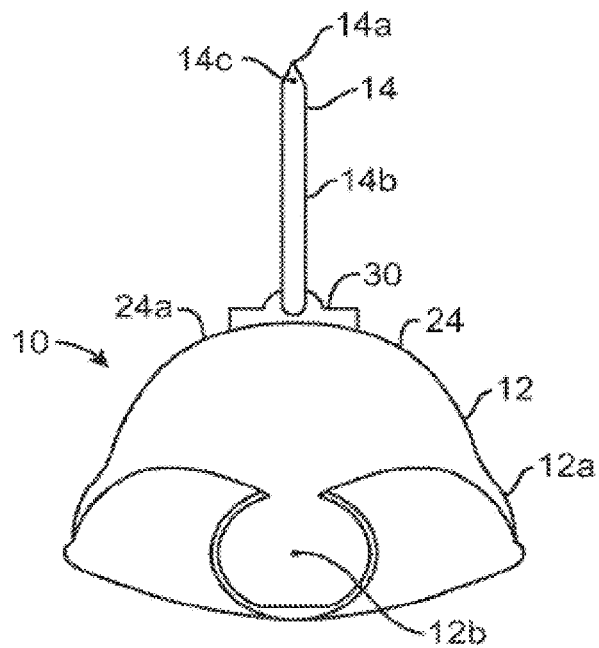
FIG. 2B is a cross-sectional view along line 2B-2B of FIG. 2A.

A pharmaceutical composition to treat the vascular disease may be delivered to the tissue surrounding a blood vessel using a drug injection or infusion catheter. In one example of a drug injection or infusion catheter as shown in FIGS. 1A-2B, a microfabricated intraluminal catheter 10 includes an actuator 12 having an actuator body 12a and central longitudinal axis 12b. The actuator body more or less forms a C-shaped outline having an opening or slit 12d extending substantially along its length. A microneedle 14 is located within the actuator body, as discussed in more detail below, when the actuator is in its unactuated condition (furled state) (FIG. 1B). The microneedle is moved outside the actuator body when the actuator is operated to be in its actuated condition (unfurled state) (FIG. 2B). The actuator may be capped at its proximal end 12e and distal end 12f by a lead end 16 and a tip end 18, respectively, of a therapeutic catheter 20. The catheter tip end serves as a means of locating the actuator inside a body lumen by use of a radio opaque coatings or markers. The catheter tip also forms a seal at the distal end 12f of the actuator. The lead end of the catheter provides the necessary interconnects (fluidic, mechanical, electrical or optical) at the proximal end 12e of the actuator.

Retaining rings 22a and 22b are located at the distal and proximal ends, respectively, of the actuator. The catheter tip is joined to the retaining ring 22a, while the catheter lead is joined to retaining ring 22b. The retaining rings are made of a thin, on the order of 10 to 100 microns (μm), substantially flexible but relatively non-distensible material, such as Parylene (types C, D or N), or a metal, for example, aluminum, stainless steel, gold, titanium or tungsten. The retaining rings form a flexible but relatively non-distensible substantially "C"-shaped structure at each end of the actuator. The catheter may be joined to the retaining rings by, for example, a butt-weld, an ultra sonic weld, integral polymer encapsulation or an adhesive such as an epoxy.

The actuator body further comprises a central, expandable section 24 located between retaining rings 22a and 22b. The expandable section 24 includes an interior open area 26 for rapid expansion when an activating fluid is supplied to that area. The central section 24 is made of a thin, semi-flexible but relatively non-distensible or flexible but relatively non-distensible, expandable material, such as a polymer, for instance, Parylene (types C, D or N), silicone, polyurethane or polyimide. The central section 24, upon actuation, is expandable somewhat like a balloon-device.

The central section is capable of withstanding pressures of up to about 200 psi upon application of the activating fluid to the open area 26. The material from which the central section is made of is flexible but relatively non-distensible or semi-flexible but relatively non-distensible in that the central section returns substantially to its original configuration and orientation (the unactuated condition) when the activating fluid is removed from the open area 26. Thus, in this sense, the central section is very much unlike a balloon which has no inherently stable structure.

The open area 26 of the actuator is connected to a delivery conduit, tube or fluid pathway 28 that extends from the catheter's lead end to the actuator's proximal end. The activating fluid is supplied to the open area via the delivery tube. The delivery tube may be constructed of Teflon© or other inert plastics. The activating fluid may be a saline solution or a radio-opaque dye.

The microneedle 14 may be located approximately in the middle of the central section 24. However, as discussed below, this is not necessary, especially when multiple microneedles are used. The microneedle is affixed to an exterior surface 24a of the central section. The microneedle is affixed to the surface 24a by an adhesive, such as cyanoacrylate. Alternatively, the microneedle maybe joined to the surface 24a by a metallic or polymer mesh-like structure 30 (See FIG. 4), which is itself affixed to the surface 24a by an adhesive. The mesh-like structure may be-made of, for instance, steel or nylon.

The microneedle includes a sharp tip 14a and a shaft 14b. The microneedle tip can provide an insertion edge or point. The shaft 14b can be hollow and the tip can have an outlet port 14c, permitting the injection of a pharmaceutical or drug into a patient. The microneedle, however, does not need to be hollow, as it may be configured like a neural probe to accomplish other tasks.

As shown, the microneedle extends approximately perpendicularly from surface 24a. Thus, as described, the microneedle will move substantially perpendicularly to an axis of a lumen into which has been inserted, to allow direct puncture or breach of body lumen walls.

The microneedle further includes a pharmaceutical or drug supply conduit, tube or fluid pathway 14d which places the microneedle in fluid communication with the appropriate fluid interconnect at the catheter lead end. This supply tube may be formed integrally with the shaft 14b, or it may be formed as a separate piece that is later joined to the shaft by, for example, an adhesive such as an epoxy.

The needle 14 may be a 30-gauge, or smaller, steel needle. Alternatively, the microneedle may be microfabricated from polymers, other metals, metal alloys or semiconductor materials. The needle, for example, may be made of Parylene, silicon or glass. Microneedles and methods of fabrication are described in U.S. application Ser. No. 09/877,653, filed Jun. 8, 2001, entitled "Microfabricated Surgical Device", assigned to the assignee of the subject application, the entire disclosure of which is incorporated herein by reference.

Figure 3:
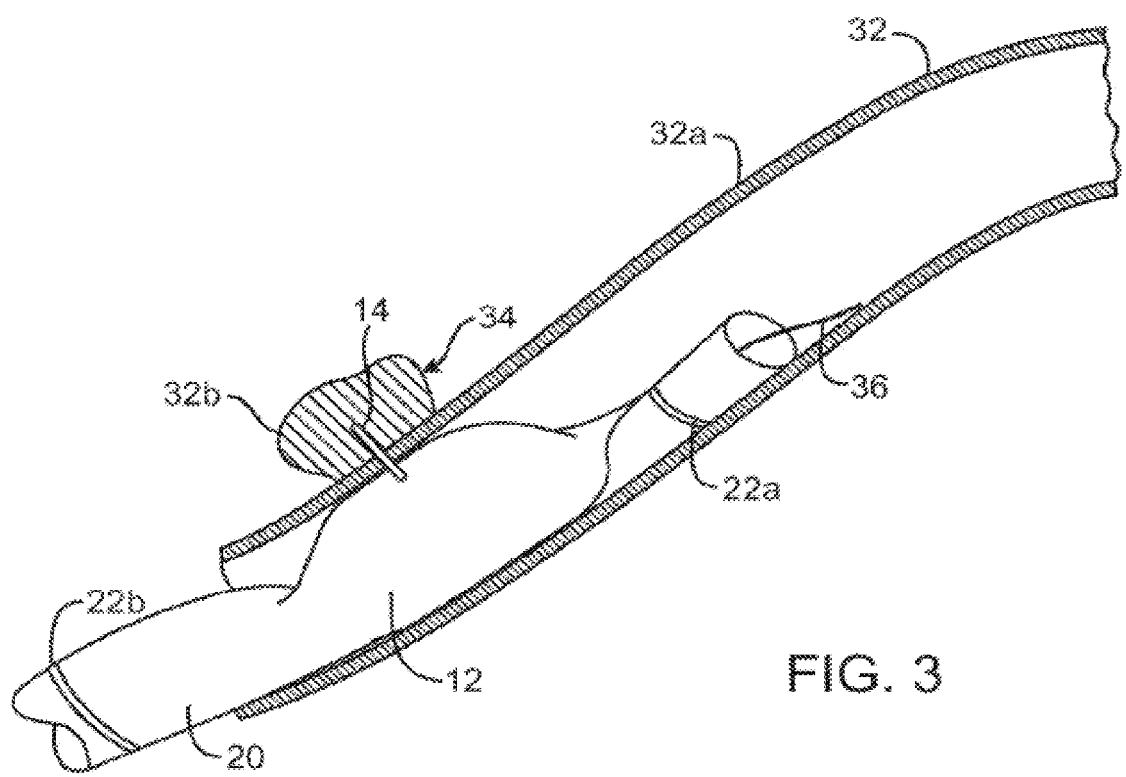
FIG. 3 is a schematic, perspective view of the intraluminal catheter of FIGS. 1A-1C injecting therapeutic agents into an adventitial space surrounding a body lumen in accordance with the methods of the present disclosure.

The catheter 20, in use, is inserted through an opening in the body (e.g. for bronchial or sinus treatment) or through a percutaneous puncture site (e.g. for artery or venous treatment) and moved within a patient's body passageways 32, until a specific, targeted region 34 is reached (see FIG. 3). The targeted region 34 may be the site of tissue damage or more usually will be adjacent the sites typically being within 100 mm or less to allow migration of the therapeutic or diagnostic agent. As is well known in catheter-based interventional procedures, the catheter 20 may follow a guide wire 36 that has previously been inserted into the patient. Optionally, the catheter 20 may also follow the path of a previously-inserted guide catheter (not shown) that encompasses the guide wire.

During maneuvering of the catheter 20, well-known methods of fluoroscopy or magnetic resonance imaging (MRI) can be used to image the catheter and assist in positioning the actuator 12 and the microneedle 14 at the target region. As the catheter is guided inside the patient's body, the microneedle remains unfurled or held inside the actuator body so that no trauma is caused to the body lumen walls.

After being positioned at the target region 34, movement of the catheter is terminated and the activating fluid is supplied to the open area 26 of the actuator, causing the expandable section 24 to rapidly unfurl, moving the microneedle 14 in a substantially perpendicular direction, relative to the longitudinal central axis 12b of the actuator body 12a, to puncture a body lumen wall 32a. It may take only between approximately 100 milliseconds and five seconds for the microneedle to move from its furled state to its unfurled state.

The ends of the actuator at the retaining rings 22a and 22b remain fixed to the catheter 20. Thus, they do not deform during actuation. Since the actuator begins as a furled structure, its so-called pregnant shape may exist as an unstable buckling mode. This instability, upon actuation, may produce a large-scale motion of the microneedle approximately perpendicular to the central axis of the actuator body, causing a rapid puncture of the body lumen wall without a large momentum transfer. As a result, a microscale opening is produced with very minimal damage to the surrounding tissue. Also, since the momentum transfer is relatively small, only a negligible bias force is required to hold the catheter and actuator in place during actuation and puncture.

The microneedle aperture, in fact, travels with such force that it can enter body lumen tissue 32b as well as the adventitia, media, or intima surrounding body lumens. Additionally, since the actuator is "parked" or stopped prior to actuation, more precise placement and control over penetration of the body lumen wall are obtained.

After actuation of the microneedle and delivery of the agents to the target region via the microneedle, the activating fluid is exhausted from the open area 26 of the actuator, causing the expandable section 24 to return to its original, furled state. This also causes the microneedle to be withdrawn from the body lumen wall. The microneedle, being withdrawn, is once again sheathed by the actuator.

Various microfabricated devices can be integrated into the needle, actuator and catheter for metering flows, capturing samples of biological tissue, and measuring pH. The device 10, for instance, could include electrical sensors for measuring the flow through the microneedle as well as the pH of the pharmaceutical being deployed. The device 10 could also include an intravascular ultrasonic sensor (IVUS) for locating vessel walls, and fiber optics, as is well known in the art, for viewing the target region. For such complete systems, high integrity electrical, mechanical and fluid connections are provided to transfer power, energy, and pharmaceuticals or biological agents with reliability.

By way of example, the microneedle may have an overall length of between about 200 and 3,000 microns (µm). The interior cross-sectional dimension of the shaft 14b and supply tube 14d may be on the order of 20 to 250 um, while the tube's and shaft's exterior cross-sectional dimension may be between about 100 and 500 µm. The overall length of the actuator body may be between about 5 and 50 millimeters (mm), while the exterior and interior cross-sectional dimensions of the actuator body can be between about 0.4 and 4 mm, and 0.5 and 5 mm, respectively. The gap or slit through which the central section of the actuator unfurls may have a length of about 4-40 mm, and a cross-sectional dimension of about 50-500 µm. The diameter of the delivery tube for the activating fluid may be about 100 µm. The catheter size may be between 1.5 and 15 French (Fr).

Variations of the present disclosure include a multiple-buckling actuator with a single supply tube for the activating fluid. The multiple-buckling actuator includes multiple needles that can be inserted into or through a lumen wall for providing injection at different locations or times.

Figure 4:
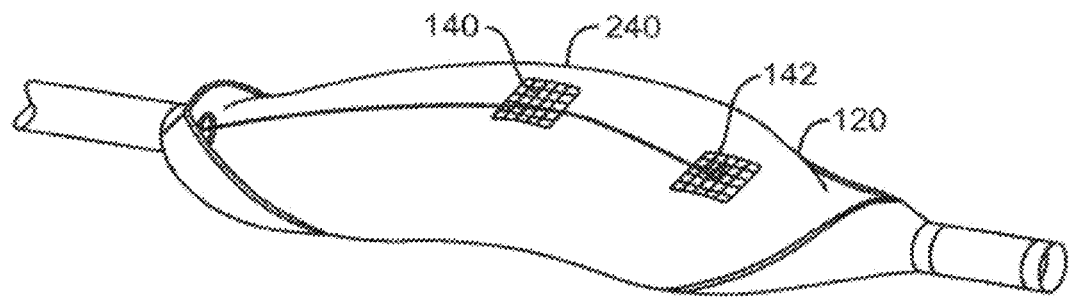
FIG. 4 is a schematic, perspective view of another embodiment of an intraluminal injection catheter useful in the methods of the present disclosure.

For instance, as shown in FIG. 4, the actuator 120 includes microneedles 140 and 142 located at different points along a length or longitudinal dimension of the central, expandable section 240. The operating pressure of the activating fluid is selected so that the microneedles move at the same time. Alternatively, the pressure of the activating fluid may be selected so that the microneedle 140 moves before the microneedle 142.

Specifically, the microneedle 140 is located at a portion of the expandable section 240 (lower activation pressure) that, for the same activating fluid pressure, will buckle outwardly before that portion of the expandable section (higher activation pressure) where the microneedle 142 is located. Thus, for example, if the operating pressure of the activating fluid within the open area of the expandable section 240 is two pounds per square inch (psi), the microneedle 140 will move before the microneedle 142. It is only when the operating pressure is increased to four psi, for instance, that the microneedle 142 will move. Thus, this mode of operation provides staged buckling with the microneedle 140 moving at time $t_1$, and pressure $p_1$, and the microneedle 142 moving at time $t_2$ and $p_2$, with $t_1$, and $p_1$, being less than $t_2$ and $p_2$, respectively.

This sort of staged buckling can also be provided with different pneumatic or hydraulic connections at different parts of the central section 240 in which each part includes an individual microneedle.

Figure 5:
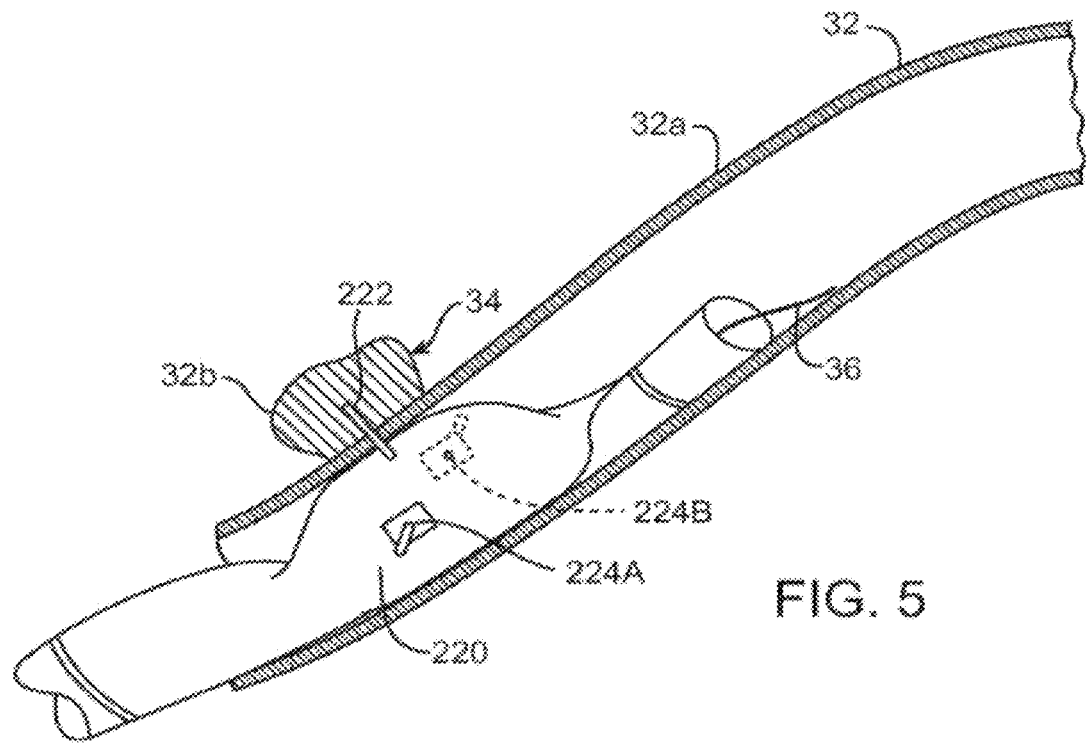
FIG. 5 is a schematic, perspective view of still another embodiment of an intraluminal injection catheter useful in the methods of the present disclosure, as inserted into one of a patient's body lumens.

Also, as shown in FIG. 5, an actuator 220 could be constructed such that its needles 222 and 224A move in different directions. As shown, upon actuation, the needles move at angle of approximately 90° to each other to puncture different parts of a lumen wall. A needle 224B (as shown in phantom) could alternatively be arranged to move at angle of about 180° to the needle 224A.

Figure 6:
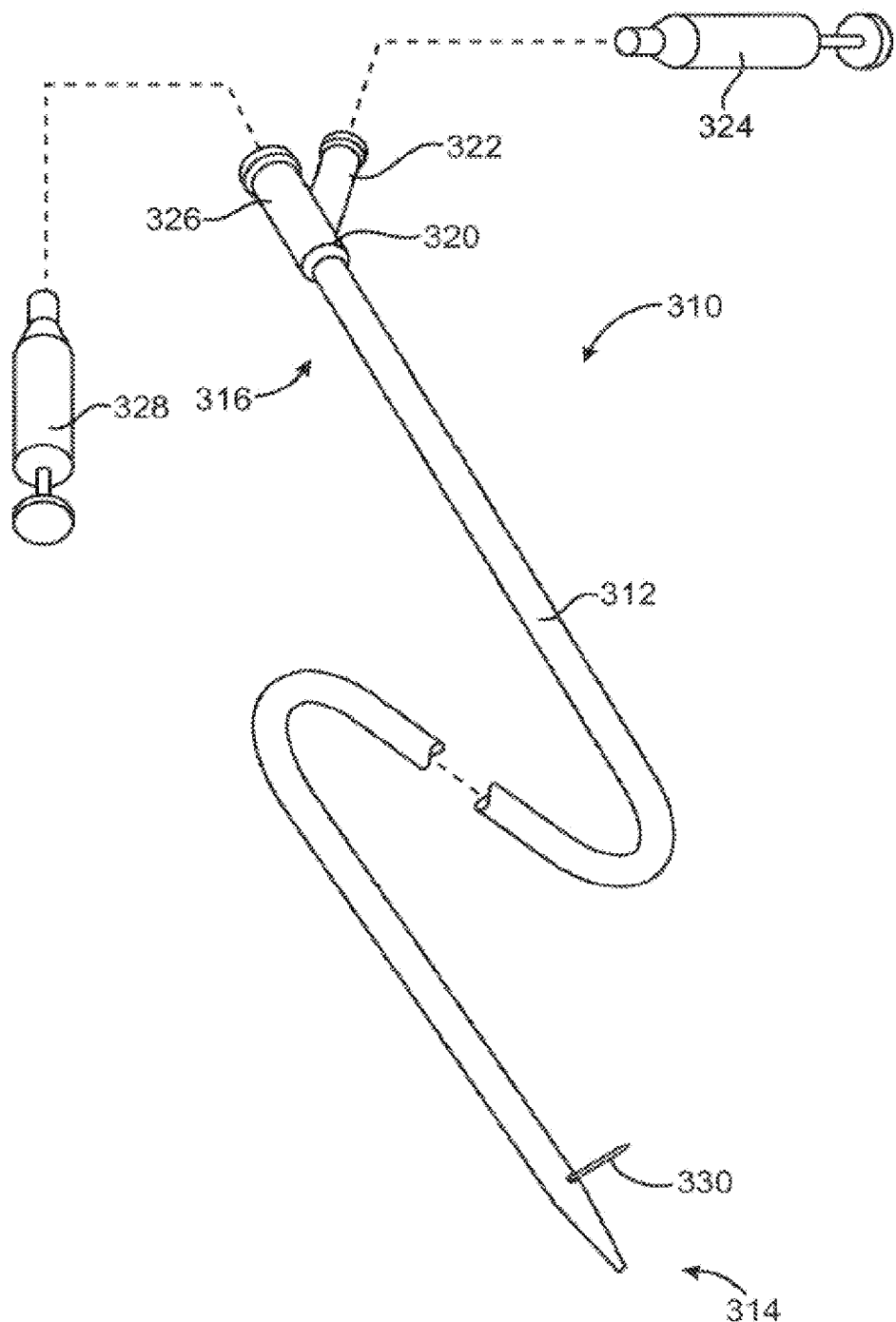
FIG. 6 is a perspective view of a needle injection catheter useful in the methods and systems of the present disclosure.

Referring now to FIG. 6, a needle injection catheter 310 constructed in accordance with the principles of the present disclosure comprises a catheter body 312 having a distal end 314 and a proximal 316. Usually, a guide wire lumen 313 will be provided in a distal nose 352 of the catheter, although over-the-wire and embodiments which do not require guide wire placement will also be within the scope of the present disclosure. A two-port hub 320 is attached to the proximal end 316 of the catheter body 312 and includes a first port 322 for delivery of a hydraulic fluid, e.g., using a syringe 324, and a second port 326 for delivering the pharmaceutical agent, e.g., using a syringe 328. A reciprocatable, deflectable needle 330 is mounted near the distal end of the catheter body 312 and is shown in its laterally advanced configuration in FIG. 6.

Figure 7:
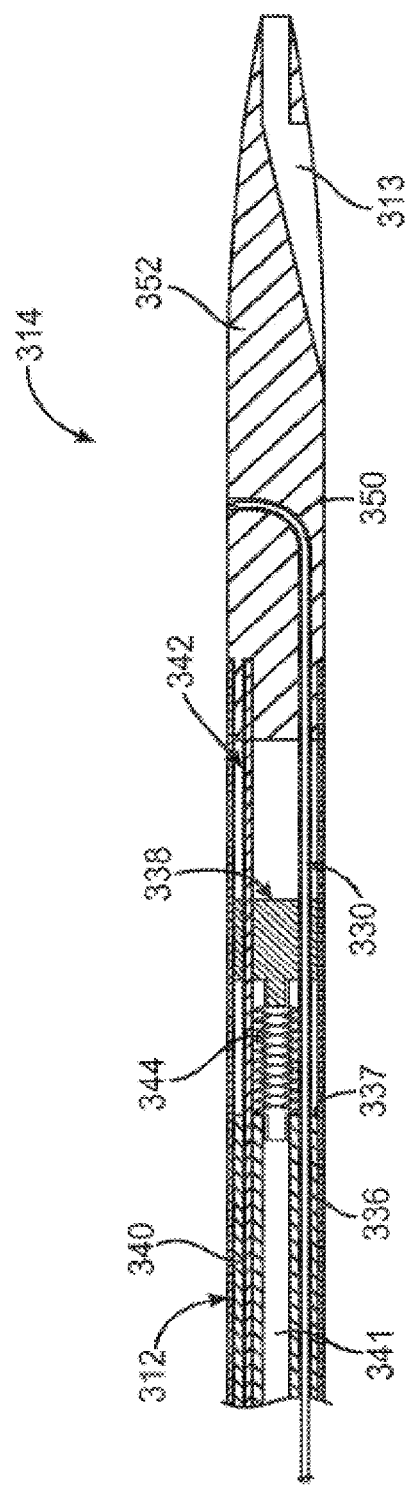
FIG. 7 is a cross-sectional view of the catheter FIG. 6 shown with the injection needle in a retracted configuration.

Referring now to FIG. 7, the proximal end 314 of the catheter body 312 has a main lumen 336 which holds the needle 330, a reciprocatable piston 338, and a hydraulic fluid delivery tube 340. The piston 338 is mounted to slide over a rail 342 and is fixedly attached to the needle 330. Thus, by delivering a pressurized hydraulic fluid through a lumen 341 tube 340 into a bellows structure 344, the piston 338 may be advanced axially toward the distal tip in order to cause the needle to pass through a deflection path 350 formed in a catheter nose 352.

Figure 8:
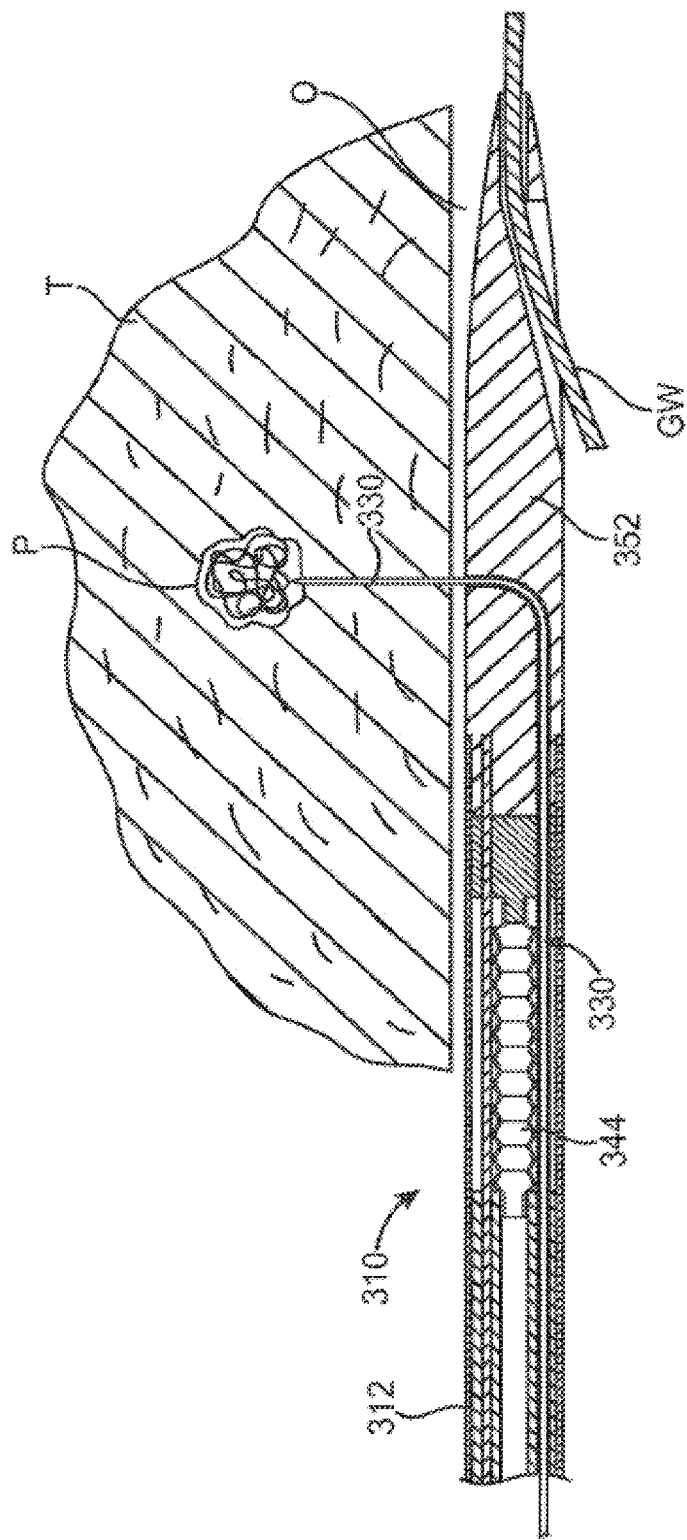
FIG. 8 is a cross-sectional view similar to FIG. 7, shown with the injection needle laterally advanced into luminal tissue for the delivery of therapeutic or diagnostic agents according to the present disclosure.

As can be seen in FIG. 8, the catheter 310 may be positioned in a coronary blood vessel BV, over a guide wire GW in a conventional manner. Distal advancement of the piston 338 causes the needle 330 to advance into luminal tissue T adjacent to the catheter when it is present in the blood vessel. The therapeutic or diagnostic agents may then be introduced through the port 326 using syringe 328 in order to introduce a plume P of agent in the cardiac tissue, as illustrated in FIG. 8. The plume P will be within or adjacent to the region of tissue damage as described above.

The needle 330 may extend the entire length of the catheter body 312 or, more usually, will extend only partially into the therapeutic or diagnostic agents delivery lumen 337 in the tube 340. A proximal end of the needle can form a sliding seal with the lumen 337 to permit pressurized delivery of the agent through the needle.

The needle 330 will be composed of an elastic material, typically an elastic or super elastic metal, typically being nitinol or other super elastic metal. Alternatively, the needle 330 could be formed from a non-elastically deformable or malleable metal which is shaped as it passes through a deflection path. The use of non-elastically deformable metals, however, is less preferred since such metals will generally not retain their straightened configuration after they pass through the deflection path.

The bellows structure 344 may be made by depositing parylene or another conformal polymer layer onto a mandrel and then dissolving the mandrel from within the polymer shell structure. Alternatively, the bellows 344 could be made from an elastomeric material to form a balloon structure. In a still further alternative, a spring structure can be utilized in, on, or over the bellows in order to drive the bellows to a closed position in the absence of pressurized hydraulic fluid therein.

After the therapeutic material is delivered through the needle 330, as shown in FIG. 8, the needle is retracted and the catheter either repositioned for further agent delivery or withdrawn. In some embodiments, the needle will be retracted simply by aspirating the hydraulic fluid from the bellows 344. In other embodiments, needle retraction may be assisted by a return spring, e.g., locked between a distal face of the piston 338 and a proximal wall of the distal tip 352 (not shown) and/or by a pull wire attached to the piston and running through lumen 341.

Figure 9A:
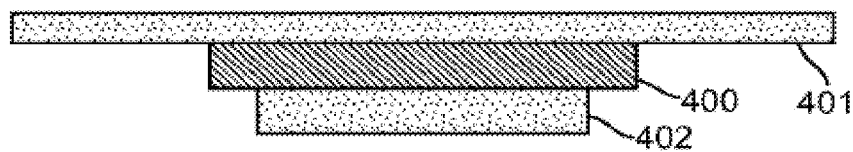
FIGS. 9A-9E are cross-sectional views of an exemplary fabrication process employed to create a free-standing low-modulus patch within a higher modulus anchor, framework or substrate.

FIGS. 9A-9E illustrate an exemplary process for fabricating a dual modulus balloon structure or anchored membrane structure in accordance with the principles of the present disclosure. The first step of the fabrication process is seen in FIG. 9A, in which a low modulus "patch", or membrane, material 400 is layered between removable (e.g. dissolvable) substrates 401 and 402. The substrate 401 covers one entire face of the patch 400, while the substrate 402 covers only a portion of the opposite face, leaving an exposed edge or border region about the periphery.

Figure 9B:
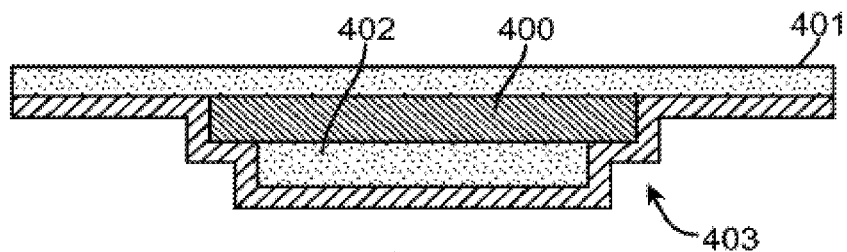

In FIG. 9B, a layer of a "flexible but relatively non-distensible" material 403 is deposited onto one side of the sandwich structure from FIG. 9A to provide a frame to which the low-modulus patch is attached. This material may be, for example, parylene N, C, or D, though it can be one of many other polymers or metals. When the flexible but relatively non-distensible material is parylene and the patch material is a silicone or siloxane polymer, a chemomechanical bond is formed between the layers, creating a strong and leak-free joint between the two materials. The joint formed between the two materials usually has a peel strength or interfacial strength of at least 0.05 N/mm$^2$, typically at least 0.1 N/mm$^2$, and often at least 0.2 N/mm$^2$.

Figure 9C:
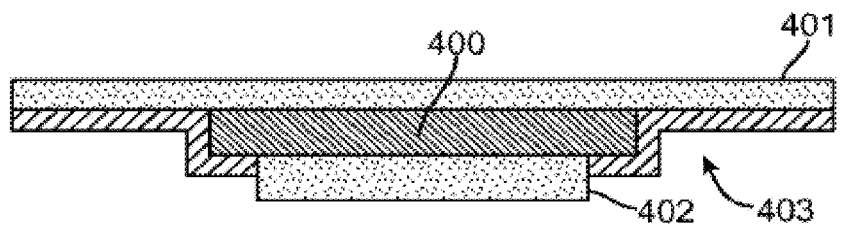
Figure 9D:
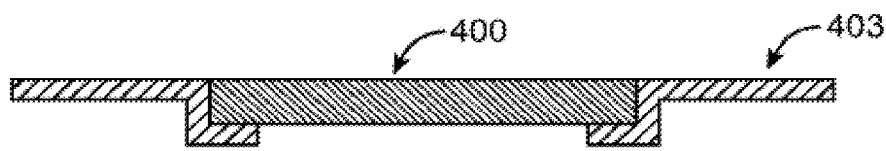

In FIG. 9C, the "flexible but relatively non-distensible" frame or anchor material 403 has been trimmed or etched to expose the substrate material 402 so that it can be removed. Materials 401 and 402 may be dissolvable polymers that can be removed by one of many chemical solvents. In FIG. 9D, the materials 401 and 402 have been removed by dissolution, leaving materials 400 and 403 joined edge-to-edge to form the low modulus, or elastomeric, patch 400 within a frame of generally flexible but relatively non-distensible material 403.

Figure 9E:
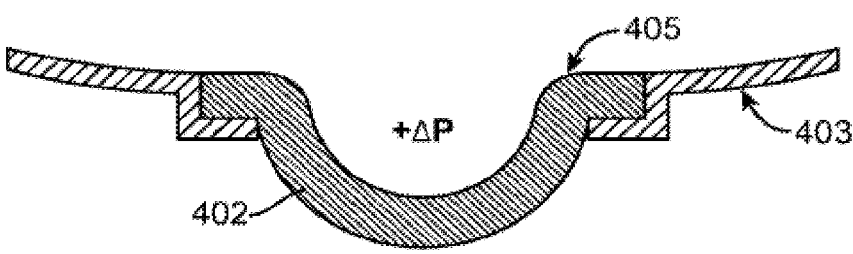

As shown in FIG. 9E, when positive pressure+$\Delta P$ is applied to one side 405 of the structure, the non-distensible frame 403 deforms only slightly, while the elastomeric patch 400 deforms much more. The low modulus material may have a material modulus which is always lower than that of the high modulus material and is typically in the range from 0.1 to 1,000 MPa, more typically in the range from 1 to 250 MPa. The high modulus material may have a material modulus in the range from 1 to 50,000 MPa, more typically in the range from 10 to 10,000 MPa. The material thicknesses may range in both cases from approximately 1 micron to several millimeters, depending on the ultimate size of the intended product. For the treatment of most body lumens, the thicknesses of both material layers 402 and 403 are in the range from 10 microns to 2 mm.

Figure 10A:
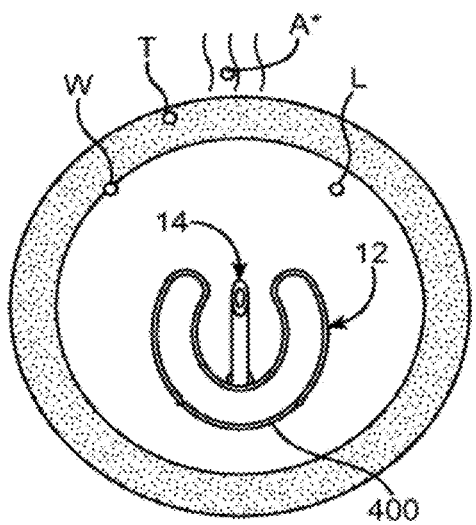
FIGS. 10A-10D are cross-sectional views of the inflation process of an intraluminal injection catheter useful in the methods of the present disclosure.

Referring to FIGS. 10A-10D, the elastomeric patch of FIGS. 9A-9D is integrated into the intraluminal catheter of FIG. 1-5. In FIG. 10A-D, the progressive pressurization of such a structure is displayed in order of increasing pressure. In FIG. 10A, the balloon is placed within a body lumen L. The lumen wall W divides the lumen from periluminal tissue T, or adventitia A*, depending on the anatomy of the particular lumen. The pressure is neutral, and the non-distensible structure forms a U-shaped involuted balloon 12 similar to that in FIG. 1 in which a needle 14 is sheathed. While a needle is displayed in this diagram, other working elements including cutting blades, laser or fiber optic tips, radiofrequency transmitters, or other structures could be substituted for the needle. For all such structures, however, the elastomeric patch 400 will usually be disposed on the opposite side of the involuted balloon 12 from the needle 14.

Figure 10B:
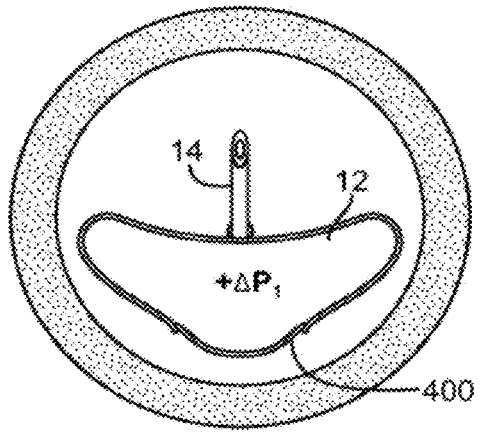
Figure 10C:
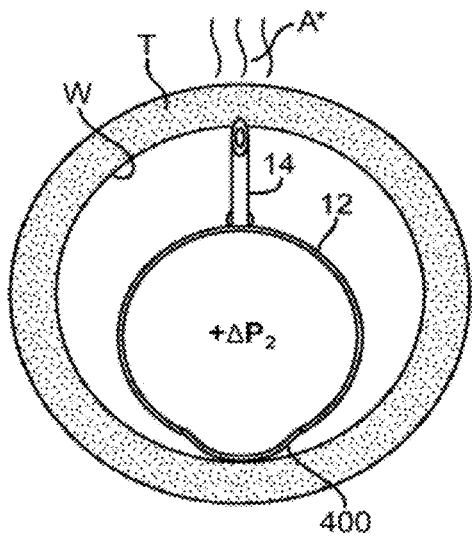
Figure 10D:
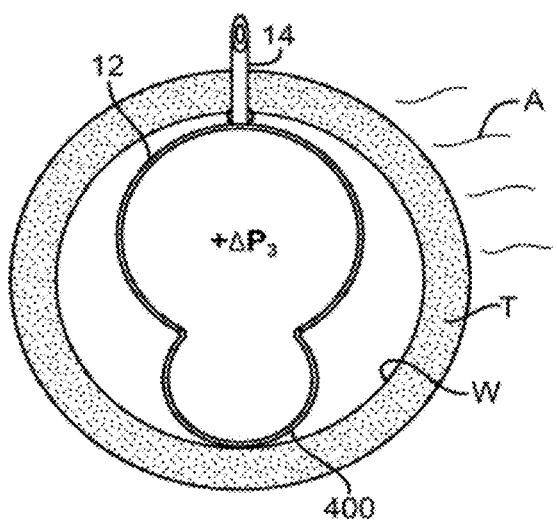

Actuation of the balloon 12 occurs with positive pressurization. In FIG. 10B, pressure (+$\Delta P_1$) is added, which begins to deform the flexible but relatively non-distensible structure, causing the balloon involution to begin its reversal toward the lower energy state of a round pressure vessel. At higher pressure+$\Delta P_2$ in FIG. 10C, the flexible but relatively non-distensible balloon material has reached its rounded shape and the elastomeric patch has begun to stretch. Finally, in FIG. 10D at still higher pressure+$\Delta P_3$, the elastomeric patch has stretched out to accommodate the full lumen diameter, providing an opposing force to the needle tip and sliding the needle through the lumen wall and into the adventitia. Typical dimensions for the body lumens contemplated in this figure are between 0.1 mm and 50 mm, more often between 0.5 mm and 20 mm, and most often between 1 mm and 10 mm. The thickness of the tissue between the lumen and adventitia is typically between 0.001 mm and 5 mm, more often between 0.01 mm and 2 mm and most often between 0.05 mm and 1 mm. The pressure+$\Delta P$ useful to cause actuation of the balloon is typically in the range from 0.1 atmospheres to 20 atmospheres, more typically in the range from 0.5 to 20 atmospheres, and often in the range from 1 to 10 atmospheres.

Figure 11C:
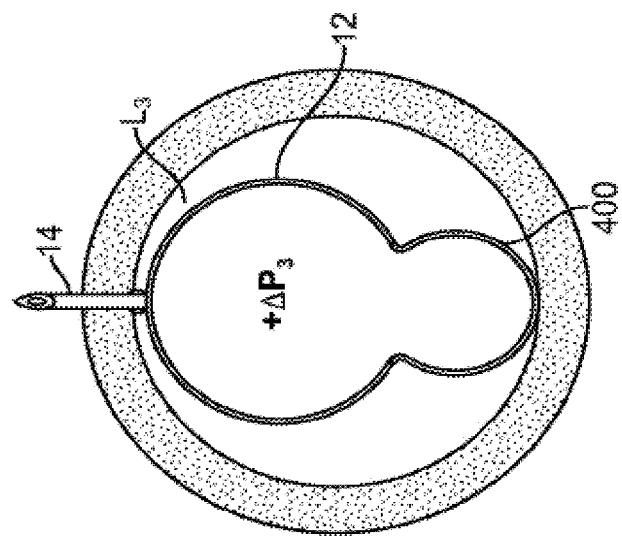
FIGS. 11A-11C are cross-sectional views of the inflated intraluminal injection catheter useful in the methods of the present disclosure, illustrating the ability to treat multiple lumen diameters.
Figure 11B:
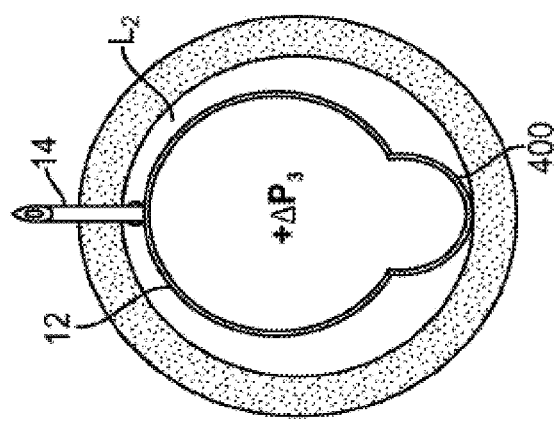
Figure 11A:
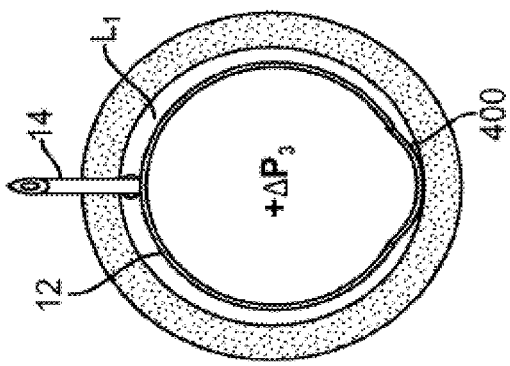

As illustrated in FIGS. 11A-11C, the dual modulus structure formed herein provides for low-pressure (i.e., below pressures that may damage body tissues) actuation of an intraluminal medical device to place working elements such as needles in contact with or through lumen walls. By inflation of a constant pressure, and the elastomeric material will conform to the lumen diameter to provide full apposition. Dual modulus balloon 12 is inflated to a pressure+$\Delta P_3$ in three different lumen diameters in FIGS. 11A, 11B, and 11C. for the progressively larger inflation of patch 400 provides optimal apposition of the needle through the vessel wall regardless of diameter. Thus, a variable diameter system is created in which the same catheter may be employed in lumens throughout the body that are within a range of diameters. This is useful because most medical products are limited to very tight constraints (typically within 0.5 mm) in which lumens they may be used. A system as described in this disclosure may accommodate several millimeters of variability in the luminal diameters for which they are useful.

Figure 12A:
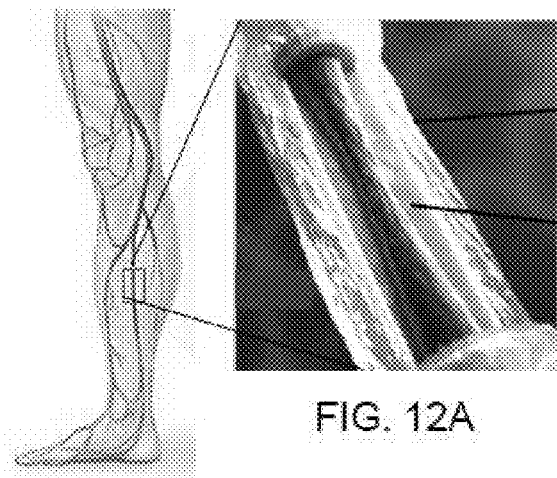
FIGS. 12A-F show schematic views of treating a blood vessel affected by atherosclerosis with delivery of a pharmaceutical composition by injection by a needle through a catheter.
Figure 12B:
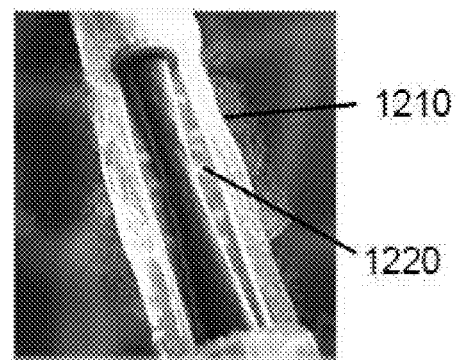
Figure 12C:
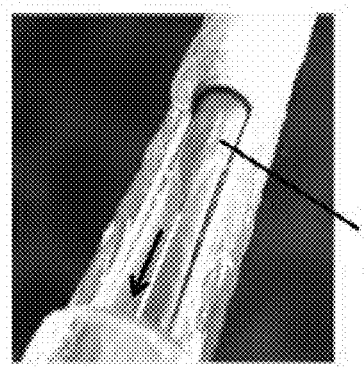
Figure 12D:
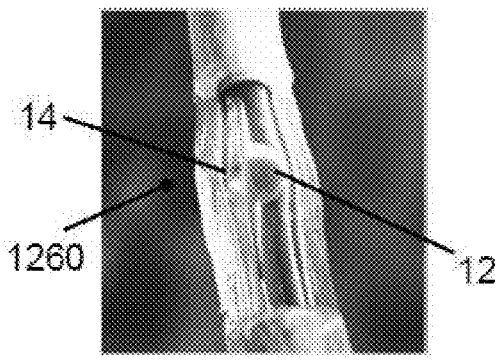
Figure 12E:
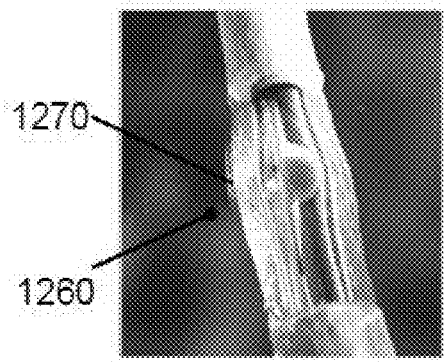
Figure 12F:
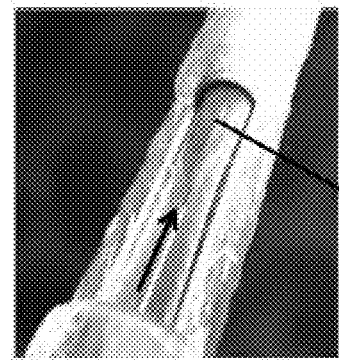

FIGS. 12A-12F show schematics of an exemplary treating vascular disease in a subject. FIG. 12A shows a blood vessel 1210 in the lower limb that may be affected by atherosclerosis or a plaque 1220 of lumen of the blood vessel. FIG. 12B shows the affected blood vessel 1210 after a revascularization procedure to increase the lumen diameter of the blood vessel. The target region of the tissue surrounding the affected blood vessel may have had a revascularization procedure previously. FIG. 12C shows the delivery of the treatment catheter 10 into the target region through the vasculature of the subject. FIG. 12D shows the expansion of the expandable element 12 of the treatment catheter to puncture into the target tissue 1260 surrounding the blood vessel with the needle 14 of the treatment catheter. The expandable element 12 may be also known as an actuator. FIG. 12E shows the delivery of the pharmaceutical composition comprising temsirolimus 1270 into the target tissue surrounding the blood vessel 1260. FIG. 12F shows the withdrawal of the treatment catheter 10 after the collapse of the expandable element 12 and withdrawal of the needle 14 from the target tissue 1260 surrounding the blood vessel.

Figure 13:
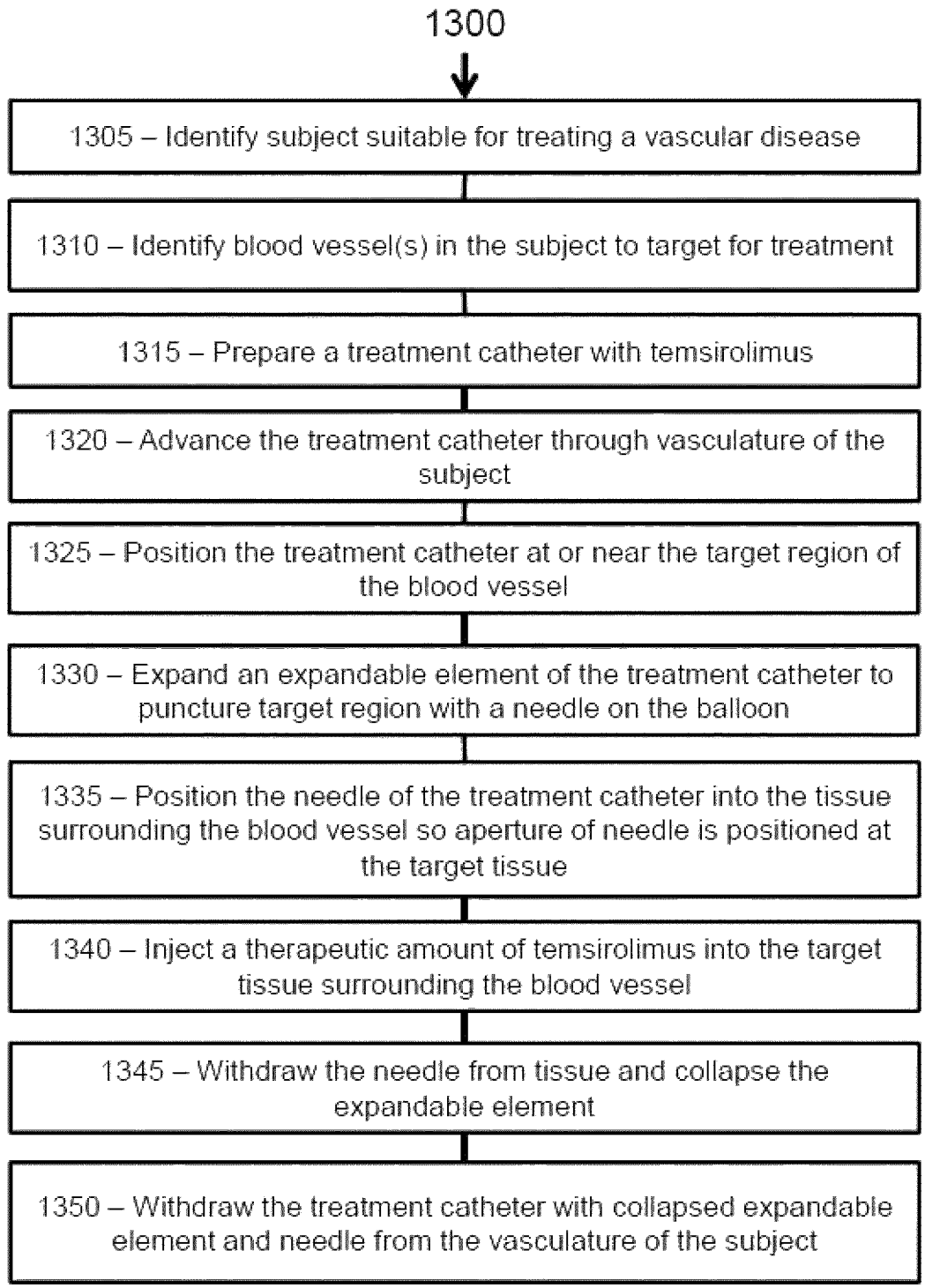
FIG. 13 shows a flow chart of a method of treating vascular disease in a subject.

FIG. 13 shows a flow chart of a method 1300 of treating vascular disease in a subject. In a step 1305, a subject suitable for treating a vascular disease may be identified. The vascular disease may be any vascular disease described above and herein. In exemplary embodiments, the vascular disease is post-angioplasty restenosis. In a step 1310, a blood vessel or blood vessels in the subject to target for treatment may be identified. The blood vessel may be any blood vessel described above and herein, such as a femoral artery. In a step 1315, a treatment catheter may be prepared with a pharmaceutical composition comprising temsirolimus. Alternative pharmaceutical compositions may be used as well; and the treatment catheter may comprise any of the drug injection and infusion devices described herein and above. In a step 1320, the catheter may be advanced through the vasculature of the subject to the target region(s), such as target region(s) in the blood vessel where plaque has been compressed by angioplasty. In a step 1325, the catheter may be positioned at or near the target region(s) of the blood vessel. In a step 1330, an expandable element of the catheter may be expanded to puncture the target region with a needle on the balloon. The expandable element may be an expandable segment, an expandable section, or a balloon of the treatment catheter. The needle may be a microneedle. In a step 1335, the needle of the treatment catheter may be positioned into the tissue surrounding the blood vessel so that the aperture of the needle may be positioned at the target tissue. In a step 1340, a therapeutic amount of the pharmaceutical composition comprising temsirolimus may be injected into the target tissue surrounding the blood vessel. The target tissue may be adventitial tissue, perivascular tissue, or connective tissue surrounding a blood vessel. In a step 1345, the needle may be withdrawn from the tissue and the expandable element may be collapsed. In a step 1350, the treatment catheter with the collapsed expandable element and the needle may be removed from the vasculature of the subject.

Although the above steps show FIG. 12 and method 1300 of treating a vascular disease in FIG. 13 in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

EXAMPLES

Example 1: Porcine Model of Femoral Vessel Injury

In a porcine model of femoral artery injury, a dose of temsirolimus was administered directly into the tissue around an injured artery through a catheter with a needle. Porcine vascular anatomy is similar to human anatomy, allowing the study of medical equipment intended for use in humans. Porcine vascular pathology allows for the development of stenotic arteries for the study of anti-stenotic or anti-restenotic therapies intended for use in humans.

In eleven Yorkshire pigs, the femoral artery in each leg (hindleg) were injured by angioplasty overstretch and followed with either temsirolimus or control saline injection, for bilateral injury and injection. The angioplasty balloon was selected to be 40-60% larger than the reference diameter of the artery to be injured and delivered by a catheter to the target injury site by carotid artery access. The angioplasty balloon was inflated to 10-20 atmosphere of pressure three times for 30 seconds each inflation at the target injury site. After the balloon was removed, the Mercator MedSystems Bullfrog® Micro-Infusion Device catheter with a needle was used to deliver either temsirolimus or control saline by injection into the adventitia and perivascular tissue around the injured artery at the center of each target injury site. The injections were administered under and verified by fluoroscopy. The animals were monitored before, during, and after the procedure, and all animals survived without adverse incidents until sacrifice.

Temsirolimus Preparation. The 25 mg/ml of Torisel® (temsirolimus) was diluted to 10 mg/ml with the supplied diluent and further diluted to 476 µg/ml in 0.9% sodium chloride solution. Then, the 476 µg/ml temsirolimus was mixed at 1:1 ratio with a contrast medium, Isovue-370, for a final temsirolimus concentration of 238 µg/ml. This temsirolimus preparation was subsequently administered in temsirolimus-treated group pigs. Similarly, a control solution was prepared by mixing 0.9% sodium chloride solution at 1:1 ratio with a contrast medium, Isovue-370. This control solution was administered in control group pigs.

Temsirolimus-Treated Group. Eight pigs received a single dose of temsirolimus (1.5 ml of 238 µg/ml temsirolimus) in the tissue around each injured femoral artery, for a total of two doses per animal. In each case, all temsirolimus treated animals underwent perivascular infusion into the femoral artery adventitia. Two pigs were sacrificed at each time point of 1 hour, 3 days, 7 days, and 28 days post-procedure, and each pig was analyzed for histopathology, pharmacokinetics, and safety evaluation.

Control Group. Three pigs served as control animals. Two of the pigs received 2 injuries per femoral vessel in multiple vessels, for a total up to 6 injury sites per animal. There were a total of 12 femoral vessels amongst the three pigs. Each injury site received 1.5 ml of 0.9% sodium chloride (saline) diluted 1:1 ratio with contrast medium (Isovue-370). One pig was sacrificed at each time point of 3 days, 7 days, and 28 days post-procedure, and each pig was analyzed for histopathology, pharmacokinetics, and safety evaluation.

All temsirolimus-treated and control group animals successfully received the respective injection administered directly to the adventitia and perivascular tissues of the femoral arteries. All injection sites except two control sites had complete or partial circumferential and longitudinal coverage of the target site by the injection.

Histopathology. There was no or minor structural injury ascribable to the overstretch angioplasty procedure at 0, 3, and 7 days. By day 28, the observed injuries were healed and produced no adverse consequences on the patency or healing of treated vessels. The temsirolimus-treated vessels were fully or nearly fully healed as early as day 7, generally showing a normal wall and occasionally displaying minimal to mild perivascular or adventitial fibrosis and low severity non-specific and localized mural inflammation considered to be of no pathological significance. There was complete or near complete re-endothelialization and no or minimal to mild and non-stenosing neointima formation.

Ki-67 staining indicated that cellular proliferation increased on day 3 in the vessel wall and adventitia and peaked on day 7 before decreasing slightly thereafter. In temsirolimus-treated vessels, a moderate to marked decrease in cell proliferation throughout the vessel wall was observed at all time periods (day 3, 7 and 28) compared to the respective controls. The decrease was substantial and consistent along the vessel length.

Figure 14A:
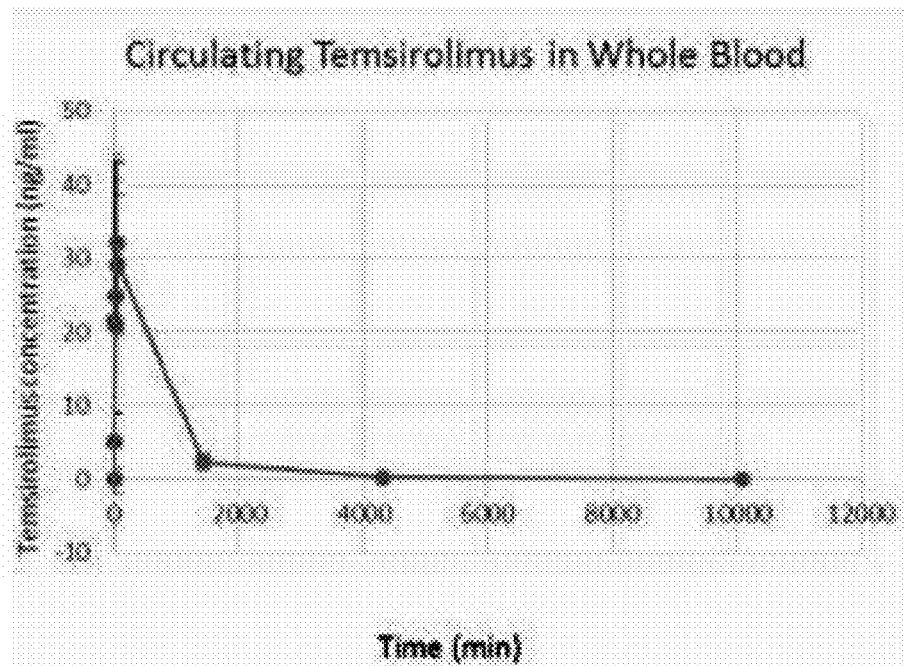
FIGS. 14A-14B are graphs showing the levels of temsirolimus and sirolimus circulating in whole blood at 1 hour, and 3, 7, and 28 days post-procedure.
Figure 14B:
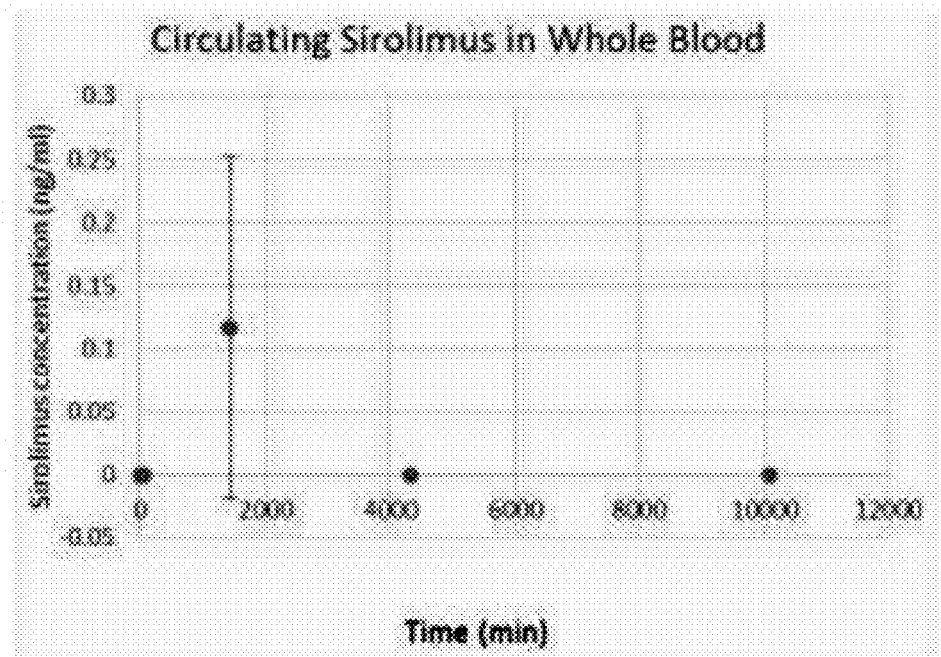
Figure 15:
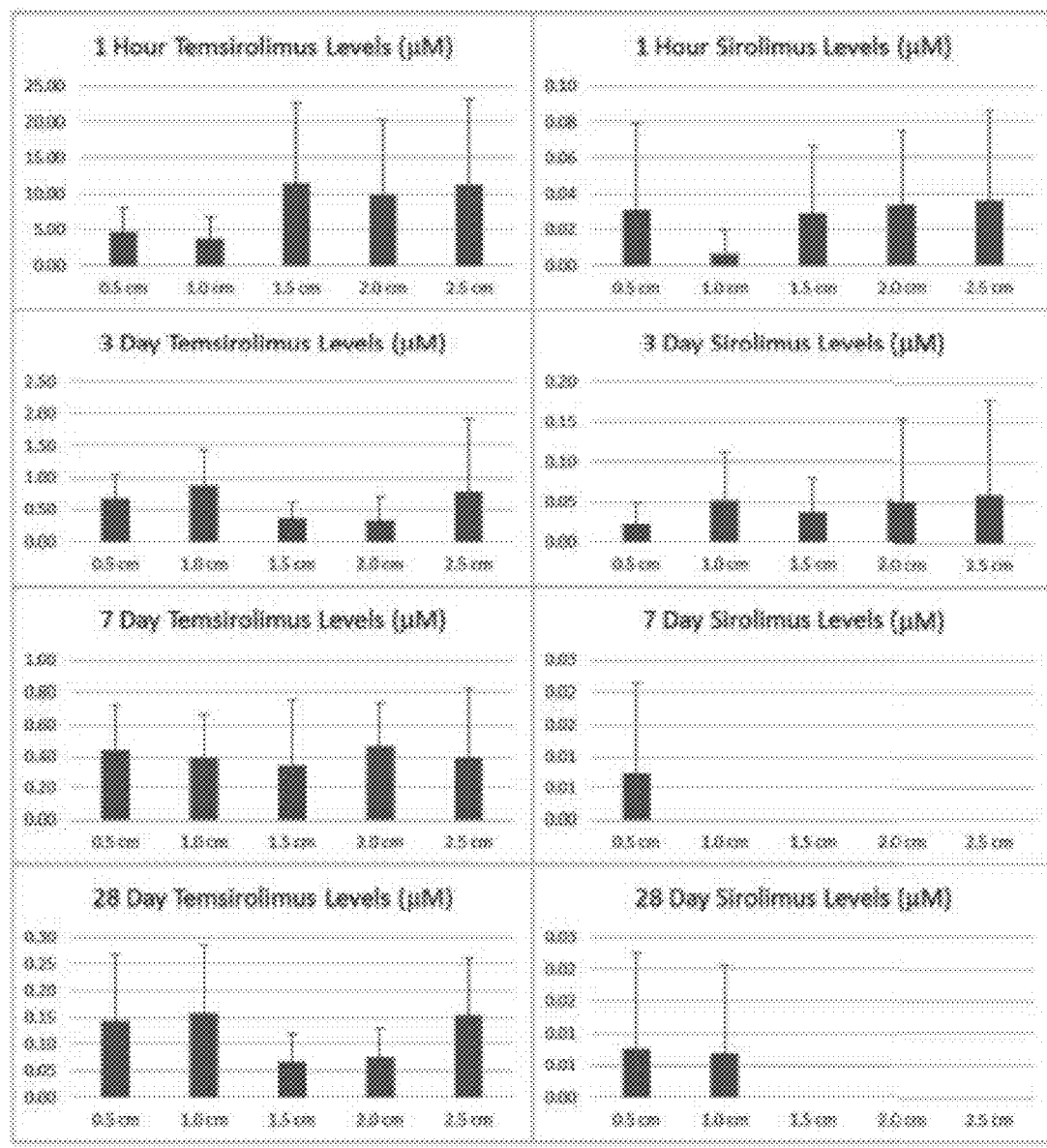
FIG. 15 includes graphs showing the levels of temsirolimus and sirolimus at 1 hour, and 3, 7, and 28 days post-procedure at various locations along the injection site (2.5 cm).

Pharmacokinetics. Whole blood samples were taken following each injection at 5 minutes, 20 minutes, 1 hour, and then 24 hours and upon sacrifice. Whole blood samples were analyzed for circulating temsirolimus and sirolimus concentrations. FIG. 14A and FIG. 14B show the levels of temsirolimus and sirolimus, respectively, circulating in whole blood at 1 hour, and 3, 7, and 28 days post-procedure. The mean temsirolimus level in whole blood was highest at 1 hour after the first injection (32.1±11.0 ng/mL) and decreased by an order of magnitude within 24 hours (2.4±1.0 ng/mL). Temsirolimus concentrations continued to decrease between 24 hours and 3 days and were below the limit of quantitation at 7 and 28 days post-procedure. FIG. 15 shows the levels of temsirolimus and sirolimus at 1 hour, and 3, 7, and 28 days post-procedure at various locations along the injection site (2.5 cm). In analysis of the harvested vessel tissues, similar trends were observed in the sirolimus concentration in the local vascular tissue, but presence of temsirolimus was much more persistent and measured in the tissue up to 28 days post-dosing. Sirolimus remained stable for three days and decreased significantly by day 7.

Safety Evaluation. There was no evidence of local or systemic toxicity assessed by clinical observations and clinical pathology either during the survival duration or by analysis of tissues post mortem. Overall injection of temsirolimus directly into the adventitia of femoral arteries with the Mercator Bullfrog® device appeared safe in this model.

This study shows that temsirolimus can be delivered safely to the adventitia and perivascular tissue in porcine models after balloon angioplasty injury of the vessel by catheter-based needle injection. In comparison to the control group, temsirolimus-treated group had reduced cellular proliferation as measured by Ki-67 expression. This may be critical for reducing restenosis in vascular disease after angioplasty or atherectomy procedures to open the blood vessel. The result of temsirolimus having inhibitory capability on vascular smooth muscle cells at and near the delivery site in a vascular disease model appears to be novel. This result suggests that temsirolimus, which has been described as a pro-drug, may be active locally to the delivery site and not only when delivered systemically and thus metabolized into the active form of sirolimus.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed in practicing the present disclosure. It is intended that the following claims define the scope of the invention and that methods and structures within the scope of these claims and their equivalents be covered thereby.

What is claimed is:

1. A method of treating a vascular disease in a subject, the method comprising:
    administering to the subject a therapeutically effective amount of a pharmaceutical composition comprising temsirolimus or a pharmaceutically acceptable salt thereof,
    wherein the composition is administered by direct injection to a disease site in a blood vessel wall or tissue surrounding the blood vessel wall,
    wherein the injection concentration of temsirolimus or the pharmaceutically acceptable salt thereof is 0.01 mg/mL to 2.0 mg/mL, and
    wherein the therapeutically effective amount of temsirolimus or the pharmaceutically acceptable salt thereof is about 0.005 mg to 5 mg per cm of longitudinal length of the disease site in the blood vessel.

2. The method of claim 1, wherein the composition is injected through a catheter with a needle.

3. The method of claim 1, wherein the composition is injected distal or proximal to the disease site.

4. The method of claim 1, wherein the composition is injected at least about 2 cm away from the disease site.

5. The method of claim 1, wherein the composition is injected at or adjacent to the disease site.

6. The method of claim 1, wherein the composition is injected into an adventitial tissue surrounding the blood vessel.

7. The method of claim 1, wherein the composition is injected into a perivascular tissue surrounding the blood vessel.

8. The method of claim 1, wherein the blood vessel is an artery.

9. The method of claim 1, wherein the blood vessel is a vein.

10. The method of claim 8, wherein the artery is a coronary artery or a peripheral artery.

11. The method of claim 8, wherein the artery is selected from the group consisting of renal artery, cerebral artery, pulmonary artery, and artery in the leg.

12. The method of claim 8, wherein the artery is below the knee.

13. The method of claim 8, wherein the artery is in the leg above the knee.

14. The method of claim 1, wherein the blood vessel is below-knee popliteal vessel or tibial vessel.

15. The method of claim 1, wherein the therapeutically effective amount of temsirolimus or the pharmaceutically acceptable salt thereof is about 1 µg to 50 mg.

16. The method of claim 15, wherein the therapeutically effective amount of temsirolimus or the pharmaceutically acceptable salt thereof is about 10 µg to 20 mg.

17. The method of claim 1, wherein the injection comprises aqueous saline.

18. The method of claim 1, wherein temsirolimus or the pharmaceutically acceptable salt thereof persists in the disease site in the blood vessel or the perivascular tissue surrounding the blood vessel wall for at least 3 days after the injection.

19. The method of claim 1, wherein the therapeutically effective amount of temsirolimus or the pharmaceutically acceptable salt thereof is about 0.025 mg to 1 mg per cm of longitudinal length of the disease site in the blood vessel.

20. The method of claim 1, wherein the injection volume of the composition is about 0.01 ml to about 50 ml.

21. The method of claim 20, wherein the injection volume of the composition is about 0.5 ml to about 20 ml.

22. The method of claim 1, wherein the injection concentration of temsirolimus or the pharmaceutically acceptable salt thereof is 0.1 mg/mL to 0.4 mg/mL.

23. The method of claim 1, wherein the injection concentration of temsirolimus or the pharmaceutically acceptable salt thereof is 0.1 mg/mL to 0.5 mg/mL.

24. The method of claim 1, wherein 12 months after administration of the pharmaceutical composition, vessel cross-sectional area at the disease site has decreased no more than 60%, when compared to vessel cross-sectional area at the disease site at the time of administration.

25. The method of claim 24, wherein 12 months after administration of the pharmaceutical composition, vessel cross-sectional area at the disease site has decreased no more than 50%, when compared to vessel cross-sectional area at the disease site at the time of administration.

26. The method of claim 25, wherein 12 months after administration of the pharmaceutical composition, vessel cross-sectional area at the disease site has decreased no more than 30%, when compared to vessel cross-sectional area at the disease site at the time of administration.

27. The method of claim 1, wherein the composition further comprises a contrast medium for visualizing the injection.

28. The method of claim 1, wherein the subject is human.

29. The method of claim 1, wherein the vascular disease is angina, myocardial infarction, congestive heart failure, cardiac arrhythmia, peripheral artery disease, claudication, or critical limb ischemia.

30. The method of claim 1, wherein the vascular disease is atherosclerosis, bypass graft failure, transplant vasculopathy, vascular restenosis, or in-stent restenosis.

31. A method of treating a peripheral artery disease in a human subject, the method comprising:
administering to the subject a therapeutically effective amount of a pharmaceutical composition comprising temsirolimus or a pharmaceutically acceptable salt thereof,
wherein the composition is administered by direct injection to or near a disease site in a tissue surrounding a wall of a peripheral artery or in the wall of the peripheral artery via a laterally extending injection needle of a catheter advanced through vasculature of the human subject,
wherein the amount of the pharmaceutical composition is therapeutically effective to cause patency at the disease site after administration to increase or minimally decrease when compared to patency at the disease site at the time of administration,
wherein the injection concentration of temsirolimus or the pharmaceutically acceptable salt thereof is 0.01 mg/mL to 2.0 mg/mL, and
wherein the therapeutically effective amount of temsirolimus or the pharmaceutically acceptable salt thereof is about 0.005 mg to 5 mg per cm of longitudinal length of the disease site in the peripheral artery.

32. The method of claim 31, wherein the therapeutically effective amount of temsirolimus or the pharmaceutically acceptable salt thereof is about 1 μg to 50 mg.

33. The method of claim 32, wherein the therapeutically effective amount of temsirolimus or the pharmaceutically acceptable salt thereof is about 10 μg to 20 mg.

34. The method of claim 31, wherein the injection comprises aqueous saline.

35. The method of claim 31, wherein temsirolimus or the pharmaceutically acceptable salt thereof persists in the disease site in the blood vessel or the perivascular tissue surrounding the blood vessel wall for at least 3 days after the injection.

36. The method of claim 31, wherein the therapeutically effective amount of temsirolimus or the pharmaceutically acceptable salt thereof is about 0.025 mg to 1 mg per cm of longitudinal length of the disease site in the peripheral artery.

37. The method of claim 31, wherein the injection volume of the composition is about 0.01 ml to about 50 ml.

38. The method of claim 37, wherein the injection volume of the composition is about 0.5 ml to about 20 ml.

39. The method of claim 31, wherein the injection concentration of temsirolimus or the pharmaceutically acceptable salt thereof is 0.1 mg/mL to 0.5 mg/mL.

40. The method of claim 39, wherein the injection concentration of temsirolimus or the pharmaceutically acceptable salt thereof is 0.1 mg/mL to 0.4 mg/mL.

41. The method of claim 31, wherein 12 months after administration of the pharmaceutical composition, vessel cross-sectional area at the disease site has decreased no more than 60%, when compared to vessel cross-sectional area at the disease site at the time of administration.

42. The method of claim 41, wherein 12 months after administration of the pharmaceutical composition, vessel cross-sectional area at the disease site has decreased no more than 50%, when compared to vessel cross-sectional area at the disease site at the time of administration.

43. The method of claim 42, wherein 12 months after administration of the pharmaceutical composition, vessel cross-sectional area at the disease site has decreased no more than 30%, when compared to vessel cross-sectional area at the disease site at the time of administration.

44. The method of claim 31, wherein the composition further comprises a contrast medium for visualizing the injection.

45. The method of claim 31, wherein the artery is below the knee.

46. The method of claim 31, wherein the artery is in the leg above the knee.

47. The method of claim 31, wherein the blood vessel is below-knee popliteal vessel or tibial vessel.

48. The method of claim 18, wherein temsirolimus or the pharmaceutically acceptable salt thereof persists in the disease site in the blood vessel or the perivascular tissue surrounding the blood vessel wall for at least 7 days after the injection.

49. The method of claim 48, wherein temsirolimus or the pharmaceutically acceptable salt thereof persists in the disease site in the blood vessel or the perivascular tissue surrounding the blood vessel wall for at least 28 days after the injection.

50. The method of claim 35, wherein temsirolimus or the pharmaceutically acceptable salt thereof persists in the disease site in the blood vessel or the perivascular tissue surrounding the blood vessel wall for at least 7 days after the injection.

51. The method of claim 50, wherein temsirolimus or the pharmaceutically acceptable salt thereof persists in the disease site in the blood vessel or the perivascular tissue surrounding the blood vessel wall for at least 28 days after the injection.

\* \* \* \* \*

UNITED STATES PATENT AND TRADEMARK OFFICE
CERTIFICATE OF CORRECTION

| | | |
|---|---|---|
| PATENT NO. | : 10,617,678 B2 | Page 1 of 1 |
| APPLICATION NO. | : 15/890857 | |
| DATED | : April 14, 2020 | |
| INVENTOR(S) | : Kirk Patrick Seward | |

It is certified that error appears in the above-identified patent and that said Letters Patent is hereby corrected as shown below:

In the Specification

Column 1, Line 13 insert:
--STATEMENT AS TO FEDERALLY SPONSORED RESEARCH
This invention was made with government support under R44HL102998 awarded by the National Heart, Lung, and Blood Institute. The government has certain rights in the invention.--

Signed and Sealed this
Twenty-first Day of November, 2023

Katherine Kelly Vidal
*Director of the United States Patent and Trademark Office*